US006780604B2

(12) United States Patent
Hsueh et al.

(10) Patent No.: US 6,780,604 B2
(45) Date of Patent: Aug. 24, 2004

(54) MAMMALIAN PRO-APOPTOTIC BOK GENES AND THEIR USES

(75) Inventors: Aaron J. W. Hsueh, Stanford, CA (US); Sheau Yu Hsu, Mountain View, CA (US)

(73) Assignee: The Board of Trustees of the Leland Stanford Junior University, Palo Alto, CA (US)

( * ) Notice: Subject to any disclaimer, the term of this patent is extended or adjusted under 35 U.S.C. 154(b) by 129 days.

(21) Appl. No.: 09/682,667

(22) Filed: Oct. 4, 2001

(65) Prior Publication Data

US 2002/0076794 A1 Jun. 20, 2002

Related U.S. Application Data

(60) Continuation of application No. 09/517,358, filed on Mar. 2, 2000, now Pat. No. 6,437,097, which is a division of application No. 09/186,250, filed on Nov. 4, 1998, now Pat. No. 6,043,055.
(60) Provisional application No. 60/064,943, filed on Nov. 7, 1997.

(51) Int. Cl.$^7$ ............................................. G01N 33/567
(52) U.S. Cl. ....................................... 435/7.21; 435/7.1
(58) Field of Search ................................... 435/7.1, 7.21

(56) References Cited

FOREIGN PATENT DOCUMENTS

WO        WO 93/11267        6/1993

OTHER PUBLICATIONS

Boyd, Janice M., et al., Bik, A Novel Death–Inducing Protein Shares A Distinct Sequence Motif With Bel–2 Family Proteins And Interacts With Viral And Cellular survival–Promoting Proteins, Oncogene (1995)vol. 11:1921–1928.
Choi, Sun Shim, et al., "A Novel Bel–2 Related Gene, Bfl–1, Is Expressed In Stomach Cancer And Preferentially Expressed In Bone Marrow," Oncogene (1995) vol. 11:1693–1698.
Chittenden, Thomas, et al., "Induction Of Apoptosis By The Bcl–2 Homologue Bak," Nature (Apr. 1995) vol. 374:733–736.
Chittenden, Thomas, et al., "A Conserved Domain in Bak, Distinct From BHI And BH2, Mediates Cell Death And Protein Binding Functions," The EMBO Journal (1995) vol. 14. No. (22): 5589–5596.
Gibson, Leonie et al., "Bcl–w, A Novel Number Of The Bcl–2 Family, Promotes Cell Survival," Oncogene (1996) vol. 13:665–675.
Hsu, Sheau Yu et al. (Nov. 1997), "Bok is a Pro–Apoptotic Bcl–2 Protein with Restricted Expression in Reproductive Tissues and Heterodimerizes with Selective Anti–Apoptotic Bcl–2 Family Members," Proc. Natl. Acad. Sci. USA, vol. 94:12401–12406.
Inohara, Naohiro, et al., "Harakiri, A Novel Regulator Of Cell Death, Encodes A Protein That Activates Apoptosis And Interacts Selectively With Survival–Promoting Proteins Bcl–2 and Bcl–X," The EMBO Journal (1997) vol. 16. No. (7):1686–1694.

Karsan, Aly, et al., "Cloning Of A Human Bcl–2 Homologue: Inflammatory Cytokines Induce Human A1 In Cultured Endothelial Cells," Blood (Apr. 15, 1996) vol. 87. No. (8): 3089–3096.
Kiefer, Michael C., et al., "Modulation Of Apoptosi By The Widely Distributed Bcl–2 Homologue Bak," Nature (Apr. 1995) vol. 374:736–739.
Kozopas, Karen M., et al., "MCL1, A Gene Expressed In Programmed Myeloid Differentiation, Has Sequence Similarity to BCL2," Proc. Natl. Acad. Sci. USA (Apr. 1993) vol. 90:3516–3520.
Oltvai, ZN, Milliman CL, Korsmeyer SJ, "BCL–2 Heterodimerizes in Vivo with a Conserved Homolog, BAX, that Accelerates Programmed Cell Death", Cell 1993, Aug. 27;74(4):609–19.
Simonian, Philip et al. (Sep. 13, 1996), "BAX Can Antagonize Bcl–X During Etoposide and Cisplatin–Induces Cell Death Independently of Its Heterodimerization with Bcl–X$_L$", The Journal of Biological Chemistry, vol. 271 (37):22764–22772.
Tsujimoto, Yoshihide, et al., "Analysis Of The Structure, Transcripts, And Protein Products Of Bcl–2, The Gene Involved In Human Follicular Lymphoma," Proc. Natl. Acad. Sci. (Jul. 1986) vol. 83:5214–5218.
White, Eileen, "Life, Death, And The Pursuit Of Apoptosis," Genes & Development (1996) vol. 10:1–15.
Yin, Xiao–Ming, et al., "BH1 and BH2 Domains Of Bcl–2 Are Required For Inhibition Of Apoptosis And Heterodimerization With Bax," Nature (May 1994) vol. 369:321–323.
GenBank Accession No. L22475 (1993).
GenBank Accession No. L22474 (1993).
GenBank Accession No. L22473 (1993).
GenBank Accession No. U76376 (1997).
GenBank Accession No. U59747 (1996).
GenBank Accession No. U29680 (1996).
GenBank Accession No. U23765 (1995).
GenBank Accession No. U34584 (1995).
GenBank Accession No. U16812 (1995).
GenBank Accession No. U27467 (1995).
GenBank Accession No. M1 3995 (1986).
GenBank Accession No. A22899 (1993).
GenBank Accession No. W77668 (1996).
Genbank Accession No. AA103989 (1996).

*Primary Examiner*—Sheela J. Huff
(74) *Attorney, Agent, or Firm*—Pamela J. Sherwood; Bozicevic, Field, & Francis LLP

(57) ABSTRACT

Nucleic acid compositions encoding a pro-apoptotic protein, Bok (Bcl-2-related ovarian killer) are identified. Bok has conserved Bcl-2 homology domains 1, 2 and 3 and a C-terminal transmembrane region present in other Bcl-2 related proteins, but lacks the BH4 domain found only in anti-apoptotic Bcl-2 proteins. Over-expression of Bok induces apoptosis. Cell killing induced by Bok is suppressed by co-expression with selective anti-apoptotic Bcl-2 proteins. Bok is highly expressed in the ovary, testis and uterus, particularly in granulosa cells, the cell type that undergoes apoptosis during follicle atresia. Identification of Bok as a new pro-apoptotic protein with wide tissue distribution and hetero-dimerization properties facilitates elucidation of apoptosis mechanisms in reproductive and other tissues, and provides a means for manipulating apoptosis.

10 Claims, 3 Drawing Sheets

SEQUENCE LISTING

<160> NUMBER OF SEQ ID NOS: 18

<210> SEQ ID NO 1
<211> LENGTH: 642
<212> TYPE: DNA
<213> ORGANISM: r. rattus

<400> SEQUENCE: 1

```
atggaggtgc tgcggcgctc ttctgtcttc gctgcggaga tcatggacgc ctttgatcgc      60
tcgcccacag acaaggagct ggtggcccag gctaaagcac taggccggga gtacgtgcac     120
gcgcggcttt tgcgcgccgg cctctcctgg agcgctccag agcgtgcctc gcctgcccct     180
ggaggacgcc tggcagaggt gtgcaccgtg ctgctgcgct gggagatga gctggagcag     240 atccgtccca gcgtatatcg gaatgtggcc cggcagctgc acatccccct gcagtctgag     300
cctgtggtga ctgatgcctt cctcgctgtg gccggccaca tcttctcagc aggtatcaca     360
tggggcaagg tagtgtccct gtactcggtg gctgcgggac tagcggtgga ctgcgtccgg     420
caagctcagc cagccatggt tcatgccctg gttgactgcc tgggggaatt tgtacgcaag     480
accctggcca cctggcttcg gaggcgtggt ggatggacgg acgtcctcaa gtgtgtggtc     540
agcacagacc ctggcttccg ctcccactgg ctcgtggcca cactctgcag ctttggccgc     600
ttcctgaagg ctgcattctt cctcctgttg ccagagagat ga                      642
```

<210> SEQ ID NO 2
<211> LENGTH: 213
<212> TYPE: PRT
<213> ORGANISM: r. rattus

<400> SEQUENCE: 2

Met Glu Val Leu Arg Arg Ser Ser Val Phe Ala Ala Glu Ile Met Asp

-continued

```
  1               5                    10                   15
Ala Phe Asp Arg Ser Pro Thr Asp Lys Glu Leu Val Ala Gln Ala Lys
             20                  25                  30

Ala Leu Gly Arg Glu Tyr Val His Ala Arg Leu Leu Arg Ala Gly Leu
         35                  40                  45

Ser Trp Ser Ala Pro Glu Arg Ala Ser Pro Ala Pro Gly Gly Arg Leu
     50                  55                  60

Ala Glu Val Cys Thr Val Leu Leu Arg Leu Gly Asp Glu Leu Glu Gln
 65                  70                  75                  80

Ile Arg Pro Ser Val Tyr Arg Asn Val Ala Arg Gln Leu His Ile Pro
                 85                  90                  95

Leu Gln Ser Glu Pro Val Val Thr Asp Ala Phe Leu Ala Val Ala Gly
             100                 105                 110

His Ile Phe Ser Ala Gly Ile Thr Trp Gly Lys Val Val Ser Leu Tyr
         115                 120                 125

Ser Val Ala Ala Gly Leu Ala Val Asp Cys Val Arg Gln Ala Gln Pro
     130                 135                 140

Ala Met Val His Ala Leu Val Asp Cys Leu Gly Glu Phe Val Arg Lys
145                 150                 155                 160

Thr Leu Ala Thr Trp Leu Arg Arg Gly Gly Trp Thr Asp Val Leu
                 165                 170                 175

Lys Cys Val Val Ser Thr Asp Pro Gly Phe Arg Ser His Trp Leu Val
             180                 185                 190

Ala Thr Leu Cys Ser Phe Gly Arg Phe Leu Lys Ala Ala Phe Phe Leu
         195                 200                 205

Leu Leu Pro Glu Arg
    210
```

<210> SEQ ID NO 3
<211> LENGTH: 513
<212> TYPE: DNA
<213> ORGANISM: r.rattus
<220> FEATURE:
<221> NAME/KEY: CDS
<222> LOCATION: (1)...(513)

<400> SEQUENCE: 3

```
atg gag gtg ctg cgg cgc tct tct gtc ttc gct gcg gag atc atg gac    48
Met Glu Val Leu Arg Arg Ser Ser Val Phe Ala Ala Glu Ile Met Asp
 1               5                  10                  15 gcc ttt gat cgc tcg ccc aca gac aag gag ctg gtg gcc cag gct aaa    96
Ala Phe Asp Arg Ser Pro Thr Asp Lys Glu Leu Val Ala Gln Ala Lys
             20                  25                  30 gca cta ggc cgg gag tac gtg cac gcg cgg ctt ttg cgc gcc ggc ctc   144
Ala Leu Gly Arg Glu Tyr Val His Ala Arg Leu Leu Arg Ala Gly Leu
         35                  40                  45 tcc tgg agc gct cca gag cgt gcc tcg cct gcc cct gga gga cgc ctg   192
Ser Trp Ser Ala Pro Glu Arg Ala Ser Pro Ala Pro Gly Gly Arg Leu
     50                  55                  60 gca gag gtg tgc acc gtg ctg ctg cgc ttg gga atc aca tgg ggc aag   240
Ala Glu Val Cys Thr Val Leu Leu Arg Leu Gly Ile Thr Trp Gly Lys
 65                  70                  75                  80 gta gtg tcc ctg tac tcg gtg gct gcg gga cta gcg gtg gac tgc gtc   288
Val Val Ser Leu Tyr Ser Val Ala Ala Gly Leu Ala Val Asp Cys Val
                 85                  90                  95 cgg caa gct cag cca gcc atg gtt cat gcc ctg gtt gac tgc ctg ggg   336
Arg Gln Ala Gln Pro Ala Met Val His Ala Leu Val Asp Cys Leu Gly
             100                 105                 110
```

```
gaa ttt gta cgc aag acc ctg gcc acc tgg ctt cgg agg cgt ggt gga      384
Glu Phe Val Arg Lys Thr Leu Ala Thr Trp Leu Arg Arg Arg Gly Gly
        115                 120                 125 tgg acg gac gtc ctc aag tgt gtg gtc agc aca gac cct ggc ttc cgc      432
Trp Thr Asp Val Leu Lys Cys Val Val Ser Thr Asp Pro Gly Phe Arg
130                 135                 140 tcc cac tgg ctc gtg gcc aca ctc tgc agc ttt ggc cgc ttc ctg aag      480
Ser His Trp Leu Val Ala Thr Leu Cys Ser Phe Gly Arg Phe Leu Lys
145                 150                 155                 160 gct gca ttc ttc ctc ctg ttg cca gag aga tga                          513
Ala Ala Phe Phe Leu Leu Leu Pro Glu Arg *
                165                 170

<210> SEQ ID NO 4
<211> LENGTH: 170
<212> TYPE: PRT
<213> ORGANISM: r.rattus

<400> SEQUENCE: 4

Met Glu Val Leu Arg Arg Ser Ser Val Phe Ala Ala Glu Ile Met Asp
1               5                   10                  15

Ala Phe Asp Arg Ser Pro Thr Asp Lys Glu Leu Val Ala Gln Ala Lys
                20                  25                  30

Ala Leu Gly Arg Glu Tyr Val His Ala Arg Leu Leu Arg Ala Gly Leu
            35                  40                  45

Ser Trp Ser Ala Pro Glu Arg Ala Ser Pro Ala Gly Gly Arg Leu
    50                  55                  60

Ala Glu Val Cys Thr Val Leu Arg Leu Gly Ile Thr Trp Gly Lys
65                  70                  75                  80

Val Val Ser Leu Tyr Ser Val Ala Ala Gly Leu Ala Val Asp Cys Val
                85                  90                  95

Arg Gln Ala Gln Pro Ala Met Val His Ala Leu Val Asp Cys Leu Gly
                100                 105                 110

Glu Phe Val Arg Lys Thr Leu Ala Thr Trp Leu Arg Arg Arg Gly Gly
            115                 120                 125

Trp Thr Asp Val Leu Lys Cys Val Val Ser Thr Asp Pro Gly Phe Arg
130                 135                 140

Ser His Trp Leu Val Ala Thr Leu Cys Ser Phe Gly Arg Phe Leu Lys
145                 150                 155                 160

Ala Ala Phe Phe Leu Leu Leu Pro Glu Arg
                165                 170

<210> SEQ ID NO 5
<211> LENGTH: 642
<212> TYPE: DNA
<213> ORGANISM: H.sapiens
<220> FEATURE:
<221> NAME/KEY: CDS
<222> LOCATION: (1)...(642)

<400> SEQUENCE: 5 atg gag gtg ctg cgg cgc tct tcg gtc ttc gct gcg gag atc atg gac       48
Met Glu Val Leu Arg Arg Ser Ser Val Phe Ala Ala Glu Ile Met Asp
1               5                   10                  15 gcc ttt gat cgc tgg ccc aca gac aag gag ctg gtg gcc cag gct aaa       96
Ala Phe Asp Arg Trp Pro Thr Asp Lys Glu Leu Val Ala Gln Ala Lys
                20                  25                  30 gca cta ggc cgg gag tac gtg cac gcg cgg ctt ttg cgc gcc ggc ctc      144
Ala Leu Gly Arg Glu Tyr Val His Ala Arg Leu Leu Arg Ala Gly Leu
```

|  |  |  |  |  |  |  |  |  |  |  |  |  |  |  |  |
|---|---|---|---|---|---|---|---|---|---|---|---|---|---|---|---|
|  |  | 35 |  |  |  | 40 |  |  |  | 45 |  |  |  |  |  |
| tcc | tgg | agc | gct | cca | gag | cgt | gcc | tcg | cct | gcc | cct | gga | gga | cgc | ctg | 192 |
| Ser | Trp | Ser | Ala | Pro | Glu | Arg | Ala | Ser | Pro | Ala | Pro | Gly | Gly | Arg | Leu |  |
|  | 50 |  |  |  | 55 |  |  |  |  | 60 |  |  |  |  |  |  |
| gca | gag | gtg | tgc | acc | gtg | ctg | ctg | cgc | ttg | gga | gat | gag | ctg | gag | cag | 240 |
| Ala | Glu | Val | Cys | Thr | Val | Leu | Leu | Arg | Leu | Gly | Asp | Glu | Leu | Glu | Gln |  |
| 65 |  |  |  | 70 |  |  |  |  | 75 |  |  |  |  | 80 |  |  |
| atc | cgt | ccc | agc | gta | tat | cgg | aat | gtg | gcc | cgg | cag | ctg | cac | atc | cct | 288 |
| Ile | Arg | Pro | Ser | Val | Tyr | Arg | Asn | Val | Ala | Arg | Gln | Leu | His | Ile | Pro |  |
|  |  |  |  | 85 |  |  |  |  | 90 |  |  |  |  | 95 |  |  |
| ctg | cag | tct | gag | cct | gtg | gtg | act | gat | gcc | ttc | ctc | gct | gtg | gcc | ggc | 336 |
| Leu | Gln | Ser | Glu | Pro | Val | Val | Thr | Asp | Ala | Phe | Leu | Ala | Val | Ala | Gly |  |
|  |  |  | 100 |  |  |  |  | 105 |  |  |  |  | 110 |  |  |  |
| cac | atc | ttc | tca | gca | ggt | atc | aca | tgg | ggc | aag | gta | gtg | tcc | ctg | tac | 384 |
| His | Ile | Phe | Ser | Ala | Gly | Ile | Thr | Trp | Gly | Lys | Val | Val | Ser | Leu | Tyr |  |
|  |  | 115 |  |  |  |  | 120 |  |  |  |  | 125 |  |  |  |  |
| tcg | gcg | gct | gcg | gga | cta | gcg | gtg | gac | tgc | gtc | cgg | caa | gct | cag | cca | 432 |
| Ser | Ala | Ala | Ala | Gly | Leu | Ala | Val | Asp | Cys | Val | Arg | Gln | Ala | Gln | Pro |  |
|  | 130 |  |  |  |  | 135 |  |  |  |  | 140 |  |  |  |  |  |
| gcc | atg | gtt | cat | gcc | ctg | gtt | gac | tgc | ctg | ggg | gaa | ttt | gta | cgc | aag | 480 |
| Ala | Met | Val | His | Ala | Leu | Val | Asp | Cys | Leu | Gly | Glu | Phe | Val | Arg | Lys |  |
| 145 |  |  |  | 150 |  |  |  |  | 155 |  |  |  |  | 160 |  |  |
| acc | ttg | gct | acc | tgg | ctt | cgg | agg | cgt | ggt | gga | tgg | acg | gac | gtc | ctc | 528 |
| Thr | Leu | Ala | Thr | Trp | Leu | Arg | Arg | Arg | Gly | Gly | Trp | Thr | Asp | Val | Leu |  |
|  |  |  | 165 |  |  |  |  | 170 |  |  |  |  | 175 |  |  |  |
| aag | tgt | gtg | gtc | agc | aca | aaa | cct | ggc | ttc | cgc | tcc | cac | tgg | ctc | gtg | 576 |
| Lys | Cys | Val | Val | Ser | Thr | Lys | Pro | Gly | Phe | Arg | Ser | His | Trp | Leu | Val |  |
|  |  | 180 |  |  |  |  | 185 |  |  |  |  | 190 |  |  |  |  |
| gcc | aca | ctc | tgc | agc | ttt | ggc | cgc | ttc | ctg | aag | gct | gca | ttc | ttc | ctc | 624 |
| Ala | Thr | Leu | Cys | Ser | Phe | Gly | Arg | Phe | Leu | Lys | Ala | Ala | Phe | Phe | Leu |  |
|  | 195 |  |  |  |  | 200 |  |  |  |  | 205 |  |  |  |  |  |
| ctg | ttg | cca | gag | aga | tga |  |  |  |  |  |  |  |  |  |  | 642 |
| Leu | Leu | Pro | Glu | Arg | * |  |  |  |  |  |  |  |  |  |  |  |
|  | 210 |  |  |  |  |  |  |  |  |  |  |  |  |  |  |  |

<210> SEQ ID NO 6
<211> LENGTH: 213
<212> TYPE: PRT
<213> ORGANISM: H.sapiens

<400> SEQUENCE: 6

Met Glu Val Leu Arg Arg Ser Ser Val Phe Ala Ala Glu Ile Met Asp
1               5                   10                  15

Ala Phe Asp Arg Trp Pro Thr Asp Lys Glu Leu Val Ala Gln Ala Lys
            20                  25                  30

Ala Leu Gly Arg Glu Tyr Val His Ala Arg Leu Leu Arg Ala Gly Leu
        35                  40                  45

Ser Trp Ser Ala Pro Glu Arg Ala Ser Pro Ala Pro Gly Gly Arg Leu
    50                  55                  60

Ala Glu Val Cys Thr Val Leu Leu Arg Leu Gly Asp Glu Leu Glu Gln
65                  70                  75                  80

Ile Arg Pro Ser Val Tyr Arg Asn Val Ala Arg Gln Leu His Ile Pro
                85                  90                  95

Leu Gln Ser Glu Pro Val Val Thr Asp Ala Phe Leu Ala Val Ala Gly
            100                 105                 110

His Ile Phe Ser Ala Gly Ile Thr Trp Gly Lys Val Val Ser Leu Tyr
        115                 120                 125

Ser Ala Ala Ala Gly Leu Ala Val Asp Cys Val Arg Gln Ala Gln Pro

```
        130                 135                 140
Ala Met Val His Ala Leu Val Asp Cys Leu Gly Glu Phe Val Arg Lys
145                 150                 155                 160

Thr Leu Ala Thr Trp Leu Arg Arg Arg Gly Gly Trp Thr Asp Val Leu
                165                 170                 175

Lys Cys Val Val Ser Thr Lys Pro Gly Phe Arg Ser His Trp Leu Val
            180                 185                 190

Ala Thr Leu Cys Ser Phe Gly Arg Phe Leu Lys Ala Ala Phe Phe Leu
        195                 200                 205

Leu Leu Pro Glu Arg
    210

<210> SEQ ID NO 7
<211> LENGTH: 513
<212> TYPE: DNA
<213> ORGANISM: H. sapiens
<220> FEATURE:
<221> NAME/KEY: CDS
<222> LOCATION: (1)...(513)

<400> SEQUENCE: 7 atg gag gtg ctg cgg cgc tct tcg gtc ttc gct gcg gag atc atg gac        48
Met Glu Val Leu Arg Arg Ser Ser Val Phe Ala Ala Glu Ile Met Asp
 1               5                  10                  15 gcc ttt gat cgc tgg ccc aca gac aag gag ctg gtg gcc cag gct aaa        96
Ala Phe Asp Arg Trp Pro Thr Asp Lys Glu Leu Val Ala Gln Ala Lys
                20                  25                  30 gca cta ggc cgg gag tac gtg cac gcg cgg ctt ttg cgc gcc ggc ctc       144
Ala Leu Gly Arg Glu Tyr Val His Ala Arg Leu Leu Arg Ala Gly Leu
            35                  40                  45 tcc tgg agc gct cca gag cgt gcc tcg cct gcc cct gga gga cgc ctg       192
Ser Trp Ser Ala Pro Glu Arg Ala Ser Pro Ala Pro Gly Gly Arg Leu
        50                  55                  60 gca gag gtg tgc acc gtg ctg ctg cgc ttg gga atc aca tgg ggc aag       240
Ala Glu Val Cys Thr Val Leu Leu Arg Leu Gly Ile Thr Trp Gly Lys
 65                  70                  75                  80 gta gtg tcc ctg tac tcg gcg gct gcg gga cta gcg gtg gac tgc gtc       288
Val Val Ser Leu Tyr Ser Ala Ala Ala Gly Leu Ala Val Asp Cys Val
                 85                  90                  95 cgg caa gct cag cca gcc atg gtt cat gcc ctg gtt gac tgc ctg ggg       336
Arg Gln Ala Gln Pro Ala Met Val His Ala Leu Val Asp Cys Leu Gly
                100                 105                 110 gaa ttt gta cgc aag acc ttg gct acc tgg ctt cgg agg cgt ggt gga       384
Glu Phe Val Arg Lys Thr Leu Ala Thr Trp Leu Arg Arg Arg Gly Gly
            115                 120                 125 tgg acg gac gtc ctc aag tgt gtg gtc agc aca aaa cct ggc ttc cgc       432
Trp Thr Asp Val Leu Lys Cys Val Val Ser Thr Lys Pro Gly Phe Arg
        130                 135                 140 tcc cac tgg ctc gtg gcc aca ctc tgc agc ttt ggc cgc ttc ctg aag       480
Ser His Trp Leu Val Ala Thr Leu Cys Ser Phe Gly Arg Phe Leu Lys
145                 150                 155                 160 gct gca ttc ttc ctc ctg ttg cca gag aga tga                           513
Ala Ala Phe Phe Leu Leu Leu Pro Glu Arg *
                165                 170

<210> SEQ ID NO 8
<211> LENGTH: 170
<212> TYPE: PRT
<213> ORGANISM: H. sapiens

<400> SEQUENCE: 8
```

```
Met Glu Val Leu Arg Arg Ser Ser Val Phe Ala Ala Glu Ile Met Asp
1               5                   10                  15

Ala Phe Asp Arg Trp Pro Thr Asp Lys Glu Leu Val Ala Gln Ala Lys
            20                  25                  30

Ala Leu Gly Arg Glu Tyr Val His Ala Arg Leu Leu Arg Ala Gly Leu
        35                  40                  45

Ser Trp Ser Ala Pro Glu Arg Ala Ser Pro Ala Pro Gly Gly Arg Leu
    50                  55                  60

Ala Glu Val Cys Thr Val Leu Leu Arg Leu Gly Ile Thr Trp Gly Lys
65              70                  75                  80

Val Val Ser Leu Tyr Ser Ala Ala Gly Leu Ala Val Asp Cys Val
                85                  90                  95

Arg Gln Ala Gln Pro Ala Met Val His Ala Leu Val Asp Cys Leu Gly
                100                 105                 110

Glu Phe Val Arg Lys Thr Leu Ala Thr Trp Leu Arg Arg Gly Gly
            115                 120                 125

Trp Thr Asp Val Leu Lys Cys Val Val Ser Thr Lys Pro Gly Phe Arg
    130                 135                 140

Ser His Trp Leu Val Ala Thr Leu Cys Ser Phe Gly Arg Phe Leu Lys
145                 150                 155                 160

Ala Ala Phe Phe Leu Leu Leu Pro Glu Arg
                165                 170

<210> SEQ ID NO 9
<211> LENGTH: 12
<212> TYPE: PRT
<213> ORGANISM: R. rattus

<400> SEQUENCE: 9

Leu Leu Arg Leu Gly Asp Glu Leu Glu Gln Ile Arg
1               5                   10

<210> SEQ ID NO 10
<211> LENGTH: 12
<212> TYPE: PRT
<213> ORGANISM: H. sapiens

<400> SEQUENCE: 10

Leu Leu Arg Leu Gly Ile Thr Trp Gly Lys Val Val
1               5                   10

<210> SEQ ID NO 11
<211> LENGTH: 13
<212> TYPE: PRT
<213> ORGANISM: Artificial Sequence
<220> FEATURE:
<223> OTHER INFORMATION: Consensus motif

<400> SEQUENCE: 11

Leu Arg Arg Ala Gly Asp Glu Phe Glu Arg Tyr Arg Arg
1               5                   10

<210> SEQ ID NO 12
<211> LENGTH: 4
<212> TYPE: PRT
<213> ORGANISM: H. sapiens

<400> SEQUENCE: 12

Thr Trp Gly Lys
1
```

```
<210> SEQ ID NO 13
<211> LENGTH: 4
<212> TYPE: PRT
<213> ORGANISM: H. sapiens

<400> SEQUENCE: 13

Asn Trp Gly Arg
 1

<210> SEQ ID NO 14
<211> LENGTH: 3
<212> TYPE: PRT
<213> ORGANISM: H. sapiens

<400> SEQUENCE: 14

Gly Asp Glu
 1

<210> SEQ ID NO 15
<211> LENGTH: 24
<212> TYPE: PRT
<213> ORGANISM: H. sapiens

<400> SEQUENCE: 15

Leu Arg Arg Ile Gly Asp Glu Leu Asp Ser Asn Ala Asp Gly Asn Phe
 1               5                  10                  15

Asn Trp Gly Arg Val Val Ala Leu
            20

<210> SEQ ID NO 16
<211> LENGTH: 24
<212> TYPE: PRT
<213> ORGANISM: H. sapiens

<400> SEQUENCE: 16

Leu Ala Ile Ile Gly Asp Asp Ile Asn Arg Arg Phe Glu Ser Gly Ile
 1               5                  10                  15

Asn Trp Gly Arg Val Val Ala Leu
            20

<210> SEQ ID NO 17
<211> LENGTH: 13
<212> TYPE: PRT
<213> ORGANISM: H. sapiens

<400> SEQUENCE: 17

Leu Arg Arg Ile Gly Asn Phe Asn Trp Gly Arg Val Val
 1               5                  10

<210> SEQ ID NO 18
<211> LENGTH: 12
<212> TYPE: PRT
<213> ORGANISM: H. sapiens

<400> SEQUENCE: 18

Leu Ala Ile Ile Gly Ile Asn Trp Gly Arg Val Val
 1               5                  10
```

MAMMALIAN PRO-APOPTOTIC BOK GENES AND THEIR USES

CROSS REFERENCE TO RELATED APPLICATIONS

This application is a Continuation of U.S. application Ser. No. 09/517,358 filed Mar. 2, 2000, now U.S. Pat. No. 6,437,097 which is a Divisional of U.S. application Ser. No. 09/186,250 filed Nov. 4, 1998, now U.S. Pat. No. 6,043,055 issued on Mar. 28, 2000, which claims benefit of U.S. Provisional Application Serial No. 60/064,943 filed Nov. 7, 1997.

FEDERAL RESEARCH STATEMENT

This invention was made with Government support under Grant No. HD-31566 awarded by the National Institutes of Health. The Government may have certain rights In this invention.

BACKGROUND OF INVENTION

Apoptosis or programmed cell death is important during embryonic development, metamorphosis, tissue renewal, hormone-induced tissue atrophy and many pathological conditions. In multi-cellular organisms, apoptosis ensures the elimination of superfluous cells including those that are generated in excess, have already completed their specific functions or are harmful to the whole organism. In reproductive tissues that are characterized by cyclic functional changes, massive cell death occurs under the control of hormonal signals. A growing body of evidence suggests that the intracellular "death program" activated during apoptosis is similar in different cell types and conserved during evolution.

Apoptosis involves two essential steps. The Bcl-2 family of proteins that consists of different anti- and pro-apoptotic members is important in the "decision" step of apoptosis. In contrast, the "execution" phase of apoptosis is mediated by the activation of caspases, cysteine proteases homologous to the C. elegans protease ced-3, that induce cell death via the proteolytic cleavage of substrates vital for cellular homeostasis. Bcl-2-related proteins act upstream from caspases in the cell death pathway and recent studies demonstrated that another C. elegans gene, ced-4, or its mammalian homolog Apaf-1 can bridge between Bcl-2/ced-9 family members and caspases.

The proto-oncogene Bcl-2 was originally isolated at the breakpoint of the t (14, 18) chromosomal translocation associated with follicular B-cell lymphoma. Over-expression of Bcl-2 suppresses apoptosis induced by a variety of agents both in vitro and in vivo. Subsequent studies identified a family of Bcl-2-related proteins possessing several conserved BH (Bcl-2 homology) domains important for homo- or hetero-dimerization between family members. In addition, a C-terminal transmembrane region for membrane anchoring is also conserved in most members. Based on their differential roles in regulating apoptosis, the Bcl-2-related proteins can be separated into anti(Bcl-2, Bcl-xL, Mcl-1, Bcl-w and Bfl-1/A1) and pro-apoptotic members (Bax, BAD, Bak, Bik, Hrk and BID). Through hetero-dimerization, the balance between pro- and anti-apoptotic proteins presumably determines cell fate. The anti-apoptotic effect of Bcl-2 is not universal, however, because Bcl-2 over-expression is not effective in blocking Fas-mediated apoptosis and the apoptosis of auto-reactive thymocytes during negative selection. Recent identification of multiple Bcl-2-related proteins suggests that selective Bcl-2 members may act in a tissue- and dimerization-specific manner.

REFERENCES

Bcl related genes are discussed in Yin et al. (1994) Nature 369:321–323; Chittenden et al. (1995) EMBO J. 14:5589–5596; and White (1996) Genes Dev. 10:1 Sequences of exemplary bcl-related genes may be accessed in Genbank. The human hrk gene has the accession no. U76376 and is described in Inohara et al. (1997) EMBO J. 16:1686–1694. The human bcl-w gene has the accession no. U59747 and is described in Gibson et al. (1996) Oncogene 13:665–675. Human A1 gene has the accession no. U29680, and is described in Karsan et al. (1996) Blood 87:3089–3096. The human Bak gene has the accession no. U23765, and is described in Chittenden et al. (1995) Nature 374:733–736. The human Bak-2 gene has the accession no. U16812, and is described in Kiefer et al. (1995) Nature 374:736–739. The human Bik gene has the accession no. U34584, and is described in Boyd et al. (1995) Oncogene 11:1921–1928. The human Bfl-1 gene has the accession no. U27467, and is described in Choi et al. (1995) Oncogene 11:1693–1698. The human bcl-2 gene has the accession no. M13995, and is described in Tsujimoto and Croce (1986) P.N.A.S. 83:5214–5218. The human Bax genes have the accession nos. L22475, L22474 and L22473, and are described in Oltvai et al. (1993) Cell 74:609–619. The EBV BHRF1 gene has the accession no. A22899, and is described in WO The human mcl-1 gene is described in Kozopas et al. (1993) P.N.A.S. 90:3516–3520, and OMIM 159552.

The EST fragment, Genbank accession no. AA103989, contains partial sequence of the 5' end of the mouse Bok gene.

SUMMARY OF INVENTION

Isolated nucleotide compositions and sequences are provided for Bok genes. The provided nucleic acids include splice variants encoding long forms of the protein, as well as short forms having a truncation that deletes all or a part of the BH3 domain. The short form of Bok and other related pro-apoptotic proteins may be naturally occurring or synthetic. These short forms induce cell killing without heterodimerization with antiapoptotic proteins.

The Bok nucleic acid compositions find use in identifying homologous or related genes; in producing compositions that modulate the expression or function of its encoded protein; for gene therapy; mapping functional regions of the protein; and in studying associated physiological pathways. In addition, modulation of the gene activity in is used for prophylactic and therapeutic purposes, such as treatment of cancer and other proliferative disorders, identification of cell type based on expression, and the like.

DETAILED DESCRIPTION

Figure 1:
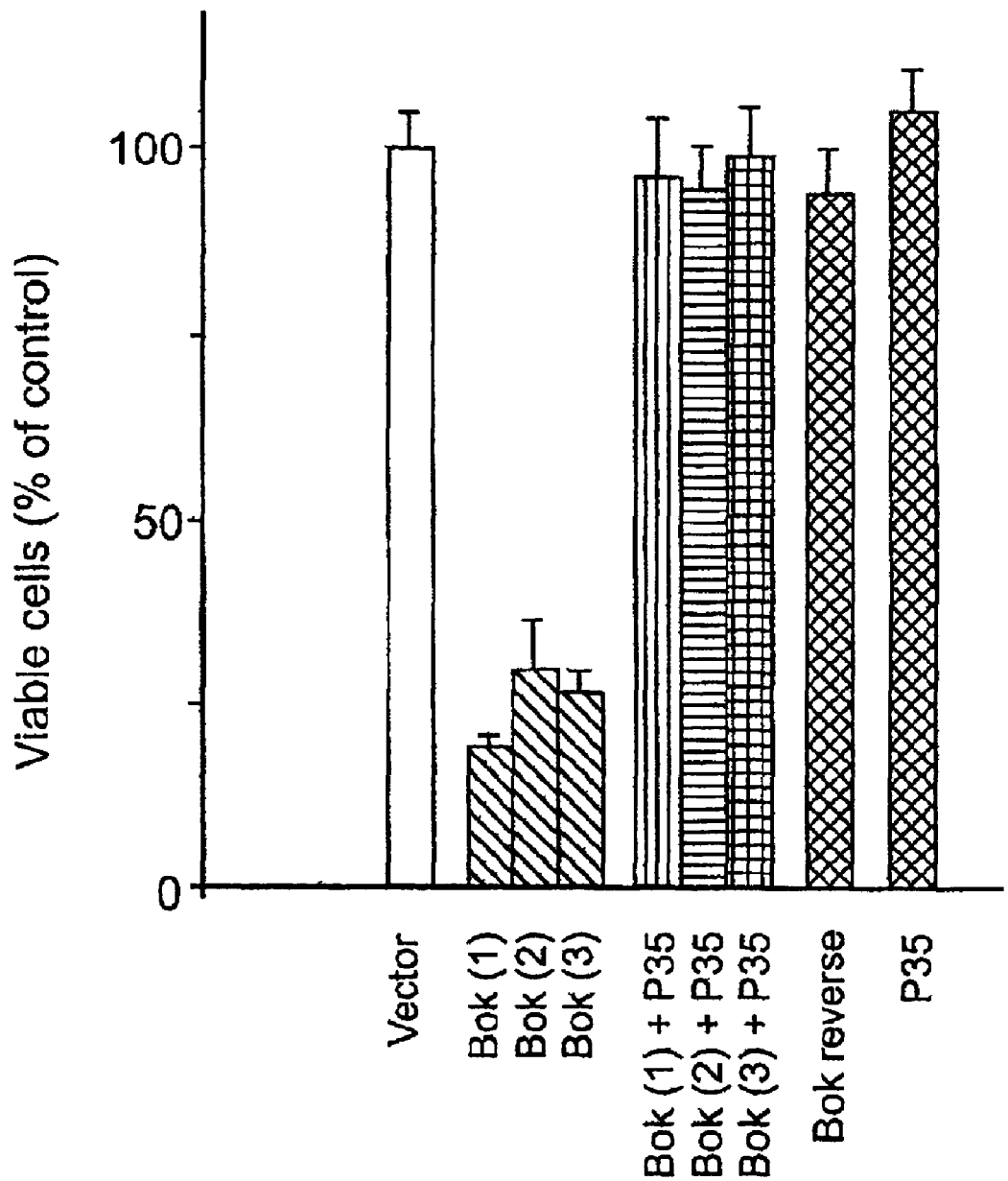
FIG. 1 is a graph showing quantitative analysis of cell killing by Bok and the inhibitory effects of P35. The number of β-gal-expressing cells (mean+/−SEM, n=3) was determined at 36 h after transfection. Data from cells transfected with three independent clones (1, 2 and 3) encoding Bok are presented. CHO cells were transfected with a total of 2.1 μg plasmid DNA including 2.0 μg of pcDNA3 expression constructs and 0.1 μg of the pCMV-β-gal reporter. In cells transfected with two different pcDNA3 expression plasmids, 1.0 μg each was used. Similar results were obtained in three separate experiments.

Nucleic acid compositions encoding Bok, a pro-apoptotic member of the bcl-2 protein family, are provided. Included are splice variants encoding long forms of the protein, as well as short forms having a truncation that deletes all or a part of the BH3 domain. Also provided are truncated forms of pro-apoptotic proteins related to Bok, e.g. Bax, Bak, etc. These short forms may be naturally occurring or synthetic. The long forms associate with anti-apoptotic proteins to form heterodimers, while the short forms induce cell killing without such heterodimerization.

As used herein, the term "Bok" is intended to generically refer to the polypeptide or nucleic acids as set forth in the Seqlist attached herewith, homologs thereof, and sequences having substantial similarity and function. Bok occurs naturally in a long form (herein Bok-L), as exemplified by the amino acid sequences provided in SEQ ID NO:2 and SEQ ID NO:6, which are rat and human, respectively. A short form (herein Bok-S) also occurs naturally, as exemplified by SEQ ID NO:4 and SEQ ID NO:8, in which there is a deletion, leading to the fusion of the N-terminal half of the BH3 domain to the C-terminal half of the BH1 domain (herein, BOK-BH3$^{inactive}$).

The term "BH3$^{inactive}$", or "BH3$^i$" is intended to generically refer to naturally occurring splice variants and synthetic variants of Bok or pro-apoptotic Bok-related proteins, e.g. Bax, Bak, etc., in which deletions or amino acid substitutions made in the BH3 domain substantially inactivate or abrogate the heterodimerization activity of the protein. These variants may also be referred to as "channel only" proteins, because they retain the ability to form channels in the mitochondria that promote apoptosis.

The BH3$^i$ variants will usually have at least less than about 50% of the anti-apoptotic protein binding activity of the parent "long" form, more usually less than about 75% of the anti-apoptotic protein binding activity, and preferably less than about 95% of anti-apoptotic protein binding activity. Examples are provided herein of BH3$^i$ variants, including but limited to: alanine substitutions at the highly conserved Bok glycine 75 residue, truncations of Bax and Bak in the BH3 domain, splice variants of Bok where there is a deletion of the amino acids 76–118; and a glycine substitution was made for leucine 71 to leucine 74 (BokGGGG: 71 LLRL 74 to 71 GGGG 74).

The BH3 domain has the consensus motif sequence: [SEQ ID NO:11} LRRAGDEFE.RYRR, and generally corresponds to the region of amino acids 71–82 in Bok (SEQ ID NO:9 and SEQ ID NO:10). A substitution at the conserved gly75 residue is shown to be sufficient for inactivation.

Modulation of pro-apoptotic gene activity, which may include Bok or other pro-apoptotic BH3$^i$ variants, in vivo is used for prophylactic and therapeutic purposes where it is desirable induce cell death in specific populations. The specificity of Bok for reproductive tissues is particularly useful in this respect. Diseases where there is hyperproliferation of reproductive tissue, e.g. uterine, testicular and ovarian carcinomas, endometriosis, squamous and glandular epithelial carcinomas of the cervix, etc. are reduced in cell number by upregulating Bok expression to cause apoptosis in susceptible cells. Expression can be regulated by introduction of exogenous Bok genes, or by inducing expression of the native gene. Introduction of exogenous Bok gene and its channel domain only variants into tumor cells following direct injection or using tumor-specific carriers can serve as effective therapies.

The isolated Bok genes are useful for in vitro, i.e. cell culture or cell-free assays, investigation of apoptosis pathways, identification of cell type based on expression, and the like. The protein is useful as an immunogen for producing specific antibodies, in screening for biologically active agents that act to regulate Bok gene expression, or that directly mimic, agonize or antagonize Bok protein function.

Characterization of Bok

Bok is expressed mainly in mammalian reproductive tissues, including ovary, testis and uterus. Bok is also expressed in diverse other tissues, albeit at lower levels. It forms a heterodimer with specific anti-apoptotic Bcl-2 proteins, including mcl-1, BHRF1 and Bfl-1. The protein—protein interaction is mediated by the conserved BH1, 2 and 3 domain regions of Bok, particularly by the BH3 domain. Overexpression of Bok induces apoptosis in certain cells, particularly reproductive cells. The rat cDNA sequence is provided as SEQ ID NO:1, the encoded polypeptide product as SEQ ID NO:2. The gene encodes a 213 amino acid polypeptide. The rat short form is provided as SEQ ID NO:3, the encoded polypeptide as SEQ ID NO:4. The nucleotide sequences of the human long and short forms are provided as SEQ ID NO:5 and 7; the encoded polypeptides as SEQ ID NO:6 and 8.

Many members of the bcl-2 gene family have been identified and characterized, as previously indicated. Other proteins in the pathway have also been identified, including caspases, and Apaf-1. The availability of isolated genes and gene products in this pathway allows the in reconstruction of the pathway and its regulation, using native or genetically altered molecules, or a combination thereof. Also of interest is the use of the genomic region 5' to Bok or related genes, particularly those members that are hormonally regulated, in order to investigate the role of particular transcription factors in regulating expression.

Identification of Bok Sequences

Homologs of Bok are identified by any of a number of methods. A fragment of the provided cDNA may be used as a hybridization probe against a cDNA library from the target organism of interest, where low stringency conditions are used. The probe may be a large fragment, or one or more short degenerate primers.

Nucleic acids having sequence similarity are detected by hybridization under low stringency conditions, for example, at 50° C. and 10×SSC (0.9 M NaCl/0.09 M sodium citrate) and remain bound when subjected to washing at 55° C. in 1×SSC. Sequence identity may be determined by hybridization under stringent conditions, for example, at 50° C. or higher and 0.1×SSC (9 mM NaCl/0.9 mM sodium citrate). Nucleic acids that are substantially identical to the provided Bok sequences, e.g. allelic variants, genetically altered versions of the gene, etc., bind to the provided Bok sequences under stringent hybridization conditions. By using probes, particularly labeled probes of DNA sequences, one can isolate homologous or related genes. The source of homologous genes may be any species, e.g. primate species, particularly human; rodents, such as rats and mice, canines, felines, bovines, ovines, equines, yeast, nematodes, etc. Between mammalian species, e.g. human and mouse, homologs have substantial sequence similarity, i.e. at least 75% sequence identity between nucleotide sequences. Sequence similarity is calculated based on a reference sequence, which may be a subset of a larger sequence, such as a conserved motif, coding region, flanking region, etc. A reference sequence will usually be at least about 18 nt long, more usually at least about 30 nt long, and may extend to the complete sequence that is being compared. Algorithms for sequence analysis are known in the art, such as BLAST, described in Altschul et al. (1990) J Mol Biol 215 :403–10. The sequences provided herein are essential for recognizing Bok related and homologous proteins in database searches.

Bok Nucleic Acid Compositions

Nucleic acids encoding Bok may be cDNA or genomic DNA or a fragment thereof. The term "Bok gene" shall be intended to mean the open reading frame encoding specific Bok polypeptides, e.g. splice variants; introns; as well as adjacent 5" and 3" non-coding nucleotide sequences involved in the regulation of expression, up to about 20 kb beyond the coding region, but possibly further in either direction. The gene may be introduced into an appropriate vector for extrachromosomal maintenance or for integration into a host genome.

The term "cDNA" as used herein is intended to include all nucleic acids that share the arrangement of sequence elements found in native mature mRNA species, where sequence elements are exons and 3" and 5" non-coding regions. Normally mRNA species have contiguous exons, with the intervening introns, when present, removed by nuclear RNA splicing, to create a continuous open reading frame encoding a Bok protein.

A genomic sequence of interest comprises the nucleic acid present between the initiation codon and the stop codon, as defined in the listed sequences, including all of the introns that are normally present in a native chromosome. It may further include the 3" and 5" untranslated regions found in the mature mRNA. It may further include specific transcriptional and translational regulatory sequences, such as promoters, enhancers, etc., including about 1 kb, but possibly more, of flanking genomic DNA at either the 5" or 3" end of the transcribed region. The genomic DNA may be isolated as a fragment of 100 kbp or smaller; and substantially free of flanking chromosomal sequence. The genomic DNA flanking the coding region, either 3' or 5', or internal regulatory sequences as sometimes found in introns, contains sequences required for proper tissue and stage specific expression.

The sequence of the 5' flanking region may be utilized for promoter elements, including enhancer binding sites, that provide for developmental regulation in tissues where Bok is expressed. The tissue specific expression is useful for determining the pattern of expression, for providing promoters that mimic the native pattern of expression, and for determination of transcription factors that regulate expression. Naturally occurring polymorphisms in the promoter region are useful for determining natural variations in expression, particularly those that may be associated with disease.

Alternatively, mutations may be introduced into the promoter region to determine the effect of altering expression in experimentally defined systems. Methods for the identification of specific DNA motifs involved in the binding of transcriptional factors are known in the art, e.g. sequence similarity to known binding motifs, gel retardation studies, etc. For examples, see Blackwell et al. (1995) Mol Med 1: 194 Mortlock et al. (1996) Genome Res. 6: 327 and Joulin and Richard (1995) Eur J Biochem 232: 620 The regulatory sequences may be used to identify cis acting sequences required for transcriptional or translational regulation of Bok expression, especially in different tissues or stages of development, and to identify cis acting sequences and trans-acting factors that regulate or mediate Bok expression. Such transcription or translational control regions may be operably linked to a Bok gene in order to promote expression of wild type or altered Bok or other proteins of interest in cultured cells, or in embryonic, fetal or adult tissues, and for gene therapy. Expression of Bok may be regulated through hormonal control.

The nucleic acid compositions of the subject invention may encode all or a part of the subject polypeptides. Double or single stranded fragments may be obtained of the DNA sequence by chemically synthesizing oligonucleotides in accordance with conventional methods, by restriction enzyme digestion, by PCR amplification, etc. For the most part, DNA fragments will be of at least 15 usually at least 18 or 25 nt, and may be at least about 50 nt. Such small DNA fragments are useful as primers for PCR, hybridization screening probes, etc. Larger DNA fragments, i.e. greater than 100 nt are useful for production of the encoded polypeptide. For use in amplification reactions, such as PCR, a pair of primers will be used. The exact composition of the primer sequences is not critical to the invention, but for most applications the primers will hybridize to the subject sequence under stringent conditions, as known in the art. It is preferable to choose a pair of primers that will generate an amplification product of at least about 50 nt, preferably at least about 100 Algorithms for the selection of primer sequences are generally known, and are available in commercial software packages. Amplification primers hybridize to complementary strands of DNA, and will prime towards each other.

The Bok genes are isolated and obtained in substantial purity, generally as other than an intact chromosome. Usually, the DNA will be obtained substantially free of other nucleic acid sequences that do not include a Bok sequence or fragment thereof, generally being at least about 50%, usually at least about 90% pure and are typically "recombinant", i.e. flanked by one or more nucleotides with which it is not normally associated on a naturally occurring chromosome.

The DNA may also be used to identify expression of the gene in a biological specimen. The manner in which one probes cells for the presence of particular nucleotide sequences, as genomic DNA or RNA, is well established in the literature and does not require elaboration here. DNA or mRNA is isolated from a cell sample. The mRNA may be amplified by RT using reverse transcriptase to form a complementary DNA strand, followed by polymerase chain reaction amplification using primers specific for the subject DNA sequences. Alternatively, the mRNA sample is separated by gel electrophoresis, transferred to a suitable support, e.g. nitrocellulose, nylon, etc., and then probed with a fragment of the subject DNA as a probe. Other techniques, such as oligonucleotide ligation assays, in situ hybridizations, and hybridization to DNA probes arrayed on a solid chip may also find use. Detection of mRNA hybridizing to the subject sequence is indicative of Bok gene expression in the sample.

The sequence of a Bok gene, including flanking promoter regions and coding regions, may be mutated in various ways known in the art to generate targeted changes in promoter strength, sequence of the encoded protein, etc. The DNA sequence or protein product of such a mutation will usually be substantially similar to the sequences provided herein, i.e. will differ by at least one nucleotide or amino acid, respectively, and may differ by at least two but not more than about ten nucleotides or amino acids. The sequence changes may be substitutions, insertions or deletions. Deletions may further include larger changes, such as deletions of a domain or exon. Of particular interest is the creation of $BH3^i$ variants. Other modifications of interest include epitope tagging, e.g. with the FLAG system, HA, etc. For studies of subcellular localization, fusion proteins with green fluorescent proteins (GFP) may be used.

Techniques for in vitro mutagenesis of cloned genes are known. Examples of protocols for site specific mutagenesis may be found in Gustin et al., *Biotechniques* 14:22 (1993); Barany, *Gene* 37:111–23 (1985); Colicelli et al., *Mol Gen Genet* 199:537–9 (1985); and Prentki et al., *Gene* 29:303–13 (1984). Methods for site specific mutagenesis can be found in Sambrook et al., *Molecular Cloning: A Laboratory Manual*, CSH Press 1989, pp. 15.3–15.108; Weiner et *Gene* 126:35–41 (1993); Sayers et al., *Biotechniques* 13:592–6 (1992); Jones and Winistorfer, *Biotechniques* 12:528–30 (1992); Barton et al., *Nucleic Acids Res* 18:7349–55 (1990); Marotti and Tomich, *Gene Anal Tech* 6:67(1989); and Zhu, *Anal Biochem* 177:120–4 (1989). Such mutated genes may be used to study structure-function relationships of Bok, or to alter properties of the protein that affect its function or regulation.

Other nucleic acids of the invention include pro-apoptotic $BH3^i$ variants. These may be synthesized by using techniques of in vitro mutagenesis and genetic engineering to inactivate the BH3 domain of Bok related genes. The wild-type sequence of these genes are known and publically available, e.g. in Genbank the human Bak gene has the accession no. U23765; human Bak-2 gene has the accession no. U16812; human Bik gene has the accession no. U34584; human Bax genes have the accession nos. L22475, L22474 and L22473. One of skill in the art can generate the physical nucleic acid from the database sequence by various means, e.g. synthesis of primers and PCR amplification, screening cDNA libraries, etc.

Bok Polypeptides

The subject nucleic acids may be employed for producing all or portions of Bok polypeptides or $BH3^i$ variants of pro-apoptotic Bok related polypeptides. For expression, an expression cassette may be employed. The expression vector will provide a transcriptional and translational initiation region, which may be inducible or constitutive, where the coding region is operably linked under the transcriptional control of the transcriptional initiation region, and a transcriptional and translational termination region. These control regions may be native to a Bok gene, or may be derived from exogenous sources.

The peptide may be expressed in prokaryotes or eukaryotes in accordance with conventional ways, depending upon the purpose for expression. For large scale production of the protein, a unicellular organism, such as *E. coli, B. subtilis, S. cerevisiae*, insect cells in combination with baculovirus vectors, or cells of a higher organism such as vertebrates, particularly mammals, e.g. COScells, may be used as the expression host cells. In some situations, it is desirable to express the Bok gene in eukaryotic cells, where the Bok protein will benefit from native folding and post-translational modifications. Small peptides can also be synthesized in the laboratory. Peptides that are subsets of the complete Bok sequence, e.g. peptides of at least about 4 amino acids, usually at least about 8 amino acids, more usually at least about 16 amino acids, up to and including functional domains, and the complete Bok polypeptide, may be used to identify and investigate parts of the protein important for function, or to raise antibodies directed against these regions.

With the availability of the protein or fragments thereof in large amounts, by employing an expression host, the protein may be isolated and purified in accordance with conventional ways. A lysate may be prepared of the expression host and the lysate purified using HPLC, exclusion chromatography, gel electrophoresis, affinity chromatography, or other purification technique. The purified protein will generally be at least about 80% pure, preferably at least about 90% pure, and may be up to and including 100% pure. Pure is intended to mean free of other proteins, as well as cellular debris.

The expressed Bok polypeptides are useful for the production of antibodies, where short fragments provide for antibodies specific for the particular polypeptide, and larger fragments or the entire protein allow for the production of antibodies over the surface of the polypeptide. Epitopes for immunization may comprise one or more of the conserved BH domains. Antibodies may be raised to the wild-type or variant forms of Bok. Antibodies may be raised to isolated peptides corresponding to these domains, or to the native protein.

Antibodies are prepared in accordance with conventional ways, where the expressed polypeptide or protein is used as an immunogen, by itself or conjugated to known immunogenic carriers, e.g. KLH, pre-S HBsAg, other viral or eukaryotic proteins, or the like. Various adjuvants may be employed, with a series of injections, as appropriate. For monoclonal antibodies, after one or more booster injections, the spleen is isolated, the lymphocytes immortalized by cell fusion, and then screened for high affinity antibody binding. The immortalized cells, i.e. hybridomas, producing the desired antibodies may then be expanded. For further description, see Monoclonal Antibodies: A Laboratory Manual, Harlow and Lane eds., Cold Spring Harbor Laboratories, Cold Spring Harbor, New York, 1988. If desired, the mRNA encoding the heavy and light chains may be isolated and mutagenized by cloning in *E. coli*, and the heavy and light chains mixed to further enhance the affinity of the antibody. Alternatives to in vivo immunization as a method of raising antibodies include binding to phage "display" libraries, usually in conjunction with in vitro affinity maturation.

Modulation of Gene Expression

The Bok genes, gene fragments, or the encoded protein or protein fragments, including $BH3^i$ variants of related pro-apoptotic sequence, are useful in gene therapy to treat disorders associated with a deficit in pro-apoptosis proteins, including different states of tumorgenesis. This approach is also useful in treating proliferative conditions of reproductive cells, such as uterine cell hyperplasia, leiomyoma and tumorigenesis. Expression vectors may be used to introduce the coding sequence into a cell. Such vectors generally have convenient restriction sites located near the promoter sequence to provide for the insertion of nucleic acid sequences. Transcription cassettes may be prepared comprising a transcription initiation region, the target gene or fragment thereof, and a transcriptional termination region. The transcription cassettes may be introduced into a variety of vectors, e.g. plasmid; retrovirus, e.g. lentivirus; adenovirus; and the like, where the vectors are able to transiently or stably be maintained in the cells, usually for a period of at least about one day, more usually for a period of at least about several days to several weeks.

The exogenous coding sequence or protein may be introduced into tissues or host cells by any number of routes, including viral infection, microinjection, or fusion of vesicles. Methods that localize the agent to the particular targeted tissues are of interest.

Antisense molecules can be used to down-regulate expression of Bok in cells. The anti-sense reagent may be antisense oligonucleotides (ODN), particularly synthetic ODN having chemical modifications from native nucleic acids, or nucleic acid constructs that express such anti-sense molecules as RNA. The antisense sequence is complementary to the mRNA of the targeted gene, and inhibits expression of the targeted gene products. Antisense molecules inhibit gene expression through various mechanisms, e.g. by reducing the amount of mRNA available for translation, through activation of RNAse H, or steric hindrance. One or a combination of antisense molecules may be administered, where a combination may comprise multiple different sequences.

Antisense molecules may be produced by expression of all or a part of the target gene sequence in an appropriate vector, where the transcriptional initiation is oriented such that an antisense strand is produced as an RNA molecule. Alternatively, the antisense molecule is a synthetic oligonucleotide. Antisense oligonucleotides will generally be at least about 7, usually at least about 12, more usually at least about 20 nucleotides in length, and not more than about 500, usually not more than about 50, more usually not more than about 35 nucleotides in length, where the length is governed by efficiency of inhibition, specificity, including absence of cross-reactivity, and the like. It has been found that short oligonucleotides, of from 7 to 8 bases in length, can be strong and selective inhibitors of gene expression (see Wagner et al. (1996) Nature Biotechnology 14 :840–844).

A specific region or regions of the endogenous sense strand mRNA sequence is chosen to be complemented by the antisense sequence. Selection of a specific sequence for the oligonucleotide may use an empirical method, where several candidate sequences are assayed for inhibition of expression of the target gene in an in vitro or animal model. A combination of sequences may also be used, where several regions of the mRNA sequence are selected for antisense complementation.

Antisense oligonucleotides may be chemically synthesized by methods known in the art (see Wagner et al. (1993) supra. and Milligan et al., supra.) Preferred oligonucleotides are chemically modified from the native phosphodiester structure, in order to increase their intracellular stability and binding affinity. A number of such modifications have been described in the literature, which alter the chemistry of the backbone, sugars or heterocyclic bases.

Among useful changes in the backbone chemistry are phosphorothioates; phosphorodithioates, where both of the non-bridging oxygens are substituted with sulfur; phosphoroamidites; alkyl phosphotriesters and boranophosphates. Achiral phosphate derivatives include 3"-O"-5"-S-phosphorothioate, 3"-S-5"-O-phosphorothioate, 3"-CH2-5"-O-phosphonate and 3"-NH-5"-O-phosphoroamidate. Peptide nucleic acids replace the entire ribose phosphodiester backbone with a peptide linkage. Sugar modifications are also used to enhance stability and affinity. The α-anomer of deoxyribose may be used, where the base is inverted with respect to the natural β-anomer. The 2"-OH of the ribose sugar may be altered to form 2"-O-methyl or 2"-O-allyl sugars, which provides resistance to degradation without comprising affinity. Modification of the heterocyclic bases must maintain proper base pairing. Some useful substitutions include deoxyuridine for deoxythymidine; 5"-deoxycytidine and 5-bromo-2"-deoxycytidine for deoxycytidine. 5propynyl-2"-deoxyuridine and 5-propynyl-2"-deoxycytidine have been shown to increase affinity and biological activity when substituted for deoxythymidine and deoxycytidine, respectively.

Genetically Altered Cell or Animal Models for Bok Function

The subject nucleic acids can be used to generate transgenic animals or site specific gene modifications in cell lines. Transgenic animals may be made through homologous recombination, where the normal Bok locus is altered. Alternatively, a nucleic acid construct is randomly integrated into the genome. Vectors for stable integration include plasmids, retroviruses and other animal viruses, YACs, and the like.

The modified cells or animals are useful in the study of pro-apoptotic gene function and regulation. For example, a series of small deletions and/or substitutions may be made in the Bok gene to determine the role of different exons in oncogenesis, signal transduction, etc. Of interest are the use of Bok to construct transgenic animal models for proliferative disorders, e.g. endometriosis, where expression of Bok is specifically reduced or absent. Specific constructs of interest include anti-sense Bok, which will block Bok expression, expression of dominant negative Bok mutations. A detectable marker, such as lac Z may be introduced into the Bok locus, where upregulation of Bok expression will result in an easily detected change in phenotype.

One may also provide for expression of the Bok gene or variants thereof in cells or tissues where it is not normally expressed or at abnormal times of development. By providing expression of Bok protein in cells in which it is not normally produced, one can induce changes in cell behavior.

DNA constructs for homologous recombination will comprise at least a portion of the Bok gene with the desired genetic modification, and will include regions of homology to the target locus. Conveniently, markers for positive and negative selection are included. Methods for generating cells having targeted gene modifications through homologous recombination are known in the art. For various techniques for transfecting mammalian cells, see Keown et al. (1990) Methods in Enzymology 185: 527–537.

For embryonic stem (ES) cells, an ES cell line may be employed, or embryonic cells may be obtained freshly from a host, e.g. mouse, rat, guinea pig, etc. Such cells are grown on an appropriate fibroblast-feeder layer or grown in the presence of leukemia inhibiting factor (LIF). When ES or embryonic cells have been transformed, they may be used to produce transgenic animals. After transformation, the cells are plated onto a feeder layer in an appropriate medium. Cells containing the construct may be detected by employing a selective medium. After sufficient time for colonies to grow, they are picked and analyzed for the occurrence of homologous recombination or integration of the construct. Those colonies that are positive may then be used for embryo manipulation and blastocyst injection. Blastocysts are obtained from 4 to 6 week old superovulated females. The ES cells are trypsinized, and the modified cells are injected into the blastocoel of the blastocyst. After injection, the blastocysts are returned to each uterine horn of pseudopregnant females. Females are then allowed to go to term and the resulting offspring screened for the construct.

By providing for a different phenotype of the blastocyst and the genetically modified cells, chimeric progeny can be readily detected.

The chimeric animals are screened for the presence of the modified gene and males and females having the modification are mated to produce homozygous progeny. If the gene alterations cause lethality at some point in development, tissues or organs can be maintained as allogeneic or congenic grafts or transplants, or in in vitro culture. The transgenic animals may be any non-human mammal, such as laboratory animals, domestic animals, etc. The transgenic animals may be used in functional studies, drug screening, etc.

In Vitro Models for Bok Function

The availability of a number of members in the bcl-2 gene family, as previously described, allows in vitro reconstruction of the apoptosis pathway. Two or more of the components may be combined in vitro, and the behavior assessed in terms of activation of transcription of specific target sequences; modification of protein components, e.g. proteolytic processing, phosphorylation, methylation, etc.; ability of different protein components to bind to each other, etc. The components may be modified by sequence deletion, substitution, etc. to determine the functional role of specific domains.

Drug screening may be performed using an in vitro model, a genetically altered cell or animal, or purified protein. One can identify ligands or substrates that bind to, modulate or mimic the action of Bok and other pro-apoptotic proteins. Areas of investigation include the development of cancer treatments, agents that modulate Bok expression, etc. Drug screening identifies agents that provide a replacement for Bok function in abnormal cells. Conversely, agents that reverse Bok function may stimulate controlled growth and healing. Of particular interest are screening assays for agents that have a low toxicity for human cells. A wide variety of assays may be used for this purpose, including labeled in vitro protein—protein binding assays, electrophoretic mobility shift assays, immunoassays for protein binding, and the like. The purified protein may also be used for determination of three-dimensional crystal structure, which can be used for modeling intermolecular interactions.

The term "agent" as used herein describes any molecule, e.g. protein or pharmaceutical, with the capability of altering or mimicking the physiological function of Bok. Generally a plurality of assay mixtures are run in parallel with different agent concentrations to obtain a differential response to the various concentrations. Typically, one of these concentrations serves as a negative control, i.e. at zero concentration or below the level of detection.

Candidate agents encompass numerous chemical classes, though typically they are organic molecules, preferably small organic compounds having a molecular weight of more than 50 and less than about 2,500 daltons. Candidate agents comprise functional groups necessary for structural interaction with proteins, particularly hydrogen bonding, and typically include at least an amine, carbonyl, hydroxyl or carboxyl group, preferably at least two of the functional chemical groups. The candidate agents often comprise cyclical carbon or heterocyclic structures and/or aromatic or polyaromatic structures substituted with one or more of the above functional groups. Candidate agents are also found among biomolecules including peptides, saccharides, fatty acids, steroids, purines, pyrimidines, derivatives, structural analogs or combinations thereof.

Candidate agents are obtained from a wide variety of sources including libraries of synthetic or natural compounds. For example, numerous means are available for random and directed synthesis of a wide variety of organic compounds and biomolecules, including expression of randomized oligonucleotides and oligopeptides. Alternatively, libraries of natural compounds in the form of bacterial, fungal, plant and animal extracts are available or readily produced. Additionally, natural or synthetically produced libraries and compounds are readily modified through conventional chemical, physical and biochemical means, and may be used to produce combinatorial libraries. Known pharmacological agents may be subjected to directed or random chemical modifications, such as acylation, alkylation, esterification, amidification, etc. to produce structural analogs.

Where the screening assay is a binding assay, one or more of the molecules may be joined to a label, where the label can directly or indirectly provide a detectable signal. Various labels include radioisotopes, fluorescers, chemiluminescers, enzymes, specific binding molecules, particles, e.g. magnetic particles, and the like. Specific binding molecules include pairs, such as biotin and streptavidin, digoxin and antidigoxin etc. For the specific binding members, the complementary member would normally be labeled with a molecule that provides for detection, in accordance with known procedures.

A variety of other reagents may be included in the screening assay. These include reagents like salts, neutral proteins, e.g. albumin, detergents, etc that are used to facilitate optimal protein—protein binding and/or reduce non-specific or background interactions. Reagents that improve the efficiency of the assay, such as protease inhibitors, nuclease inhibitors, anti-microbial agents, etc. may be used. The mixture of components are added in any order that provides for the requisite binding. Incubations are performed at any suitable temperature, typically between 4 and 40° C. Incubation periods are selected for optimum activity, but may also be optimized to facilitate rapid high-throughput screening. Typically between 0.1 and 1 hours will be sufficient.

Other assays of interest detect agents that mimic Bok function. For example, an expression construct comprising a Bok gene may be introduced into a cell line under conditions that allow expression. The level of Bok activity is determined by a functional assay. In one screening assay, candidate agents are added, and the ability to down-regulate its activity is detected. In another assay, the ability of candidate agents to enhance Bok function is determined. Alternatively, candidate agents are added to a cell that lacks functional Bok, and screened for the ability to reproduce Bok in a functional assay.

The compounds having the desired pharmacological activity may be administered in a physiologically acceptable carrier to a host for treatment of proliferative diseases, etc. The compounds may also be used to enhance Bok function. The inhibitory agents may be administered in a variety of ways, orally, topically, parenterally e.g. subcutaneously, intraperitoneally, by viral infection, intravascularly, etc. Topical treatments are of particular interest. Depending upon the manner of introduction, the compounds may be formulated in a variety of ways. The concentration of therapeutically active compound in the formulation may vary from about 0.1 The pharmaceutical compositions can be prepared in various forms, such as granules, tablets, pills, suppositories, capsules, suspensions, salves, lotions and the like. Pharmaceutical grade organic or inorganic carriers and/or diluents suitable for oral and topical use can be used to make up compositions containing the therapeutically-active compounds. Diluents known to the art include aqueous media, vegetable and animal oils and fats. Stabilizing agents, wetting and emulsifying agents, salts for varying the osmotic pressure or buffers for securing an adequate pH value, and skin penetration enhancers can be used as auxiliary agents.

Diagnostic Uses

The subject nucleic acid and/or polypeptide compositions may be used to analyze a patient sample for the presence of polymorphisms associated with a disease state or genetic predisposition to a disease state. Biochemical studies may be performed to determine whether a sequence polymorphism in a Bok coding region or control regions is associated with disease. Disease associated polymorphisms may include deletion or truncation of the gene, mutations that alter expression level, etc. Changes in the promoter or enhancer sequence that may affect expression levels of Bok can be compared to expression levels of the normal allele by various methods known in the art. Methods for determining promoter or enhancer strength include quantitation of the expressed natural protein; insertion of the variant control element into a vector with a reporter gene such as α galactosidase, luciferase, chloramphenicol acetyltransferase, etc. that provides for convenient quantitation; and the like.

A number of methods are available for analyzing nucleic acids for the presence of a specific sequence, e.g. a disease associated polymorphism. Where large amounts of DNA are available, genomic DNA is used directly. Alternatively, the region of interest is cloned into a suitable vector and grown in sufficient quantity for analysis. Cells that express Bok may be used as a source of mRNA, which may be assayed directly or reverse transcribed into cDNA for analysis. The nucleic acid may be amplified by conventional techniques, such as the polymerase chain reaction (PCR), to provide sufficient amounts for analysis. The use of the polymerase chain reaction is described in Saiki, et al. (1985) Science 239:487, and a review of techniques may be found in Sambrook, et al. Molecular Cloning: A Laboratory Manual, CSH Press 1989, pp.14.214.33. Alternatively, various methods are known in the art that utilize oligonucleotide ligation as a means of detecting polymorphisms, for examples see Riley et al. (1990) N.A.R. 18:2887–2890; and Delahunty et al. (1996) Am. J. Hum. Genet. 58:1239–1246.

A detectable label may be included in an amplification reaction. Suitable labels include fluorochromes, e.g. fluorescein isothiocyanate (FITC), rhodamine, Texas Red, phycoerythrin, allophycocyanin, 6-carboxyfluorescein (6-FAM), 2",7"",5"-dichloro-6-carboxyfluorescein (JOE), 6-carboxy-X-rhodamine (ROX), 6",4",7",4,7-hexachloroflourescein (HEX), 5(5 or N, N,N",N"-tetramethyl-6-carboxyrhodamine (TAMRA), radioactive labels, e.g. $^{35}P$, $^{35}S$, $^{3}H$; etc. The label may be a two stage system, where the amplified DNA is conjugated to biotin, haptens, etc. having a high affinity binding partner, e.g. avidin, specific antibodies, etc., where the binding partner is conjugated to a detectable label. The label may be conjugated to one or both of the primers. Alternatively, the pool of nucleotides used in the amplification is labeled, so as to incorporate the label into the amplification product.

The sample nucleic acid, e.g. amplified or cloned fragment, is analyzed by one of a number of methods known in the art. The nucleic acid may be sequenced by dideoxy or other methods, and the sequence of bases compared to a wild-type Bok sequence. Hybridization with the variant sequence may also be used to determine its presence, by Southern blots, dot blots, etc. The hybridization pattern of a control and variant sequence to an array of oligonucleotide probes immobilised on a solid support, as described in U.S. Pat. No. 5,445,934, or in WO95/35505, may also be used as a means of detecting the presence of variant sequences. Single strand conformational polymorphism (SSCP) analysis, denaturing gradient gel electrophoresis (DGGE), and heteroduplex analysis in gel matrices are used to detect conformational changes created by DNA sequence variation as alterations in electrophoretic mobility. Alternatively, where a polymorphism creates or destroys a recognition site for a restriction endonuclease, the sample is digested with that endonuclease, and the products size fractionated to determine whether the fragment was digested. Fractionation is performed by gel or capillary electrophoresis, particularly acrylamide or agarose gels.

Screening for mutations in Bok may be based on the functional or antigenic characteristics of the protein. Protein truncation assays are useful in detecting deletions that may affect the biological activity of the protein. Various immunoassays designed to detect polymorphisms in Bok proteins may be used in screening. Where many diverse genetic mutations lead to a particular disease phenotype, functional protein assays have proven to be effective screening tools. The activity of the encoded Bok protein may be determined by comparison with the wild-type protein.

Antibodies specific for a Bok may be used in staining or in immunoassays. Samples, as used herein, include biological fluids such as semen, blood, cerebrospinal fluid, tears, saliva, lymph, dialysis fluid and the like; organ or tissue culture derived fluids; and fluids extracted from physiological tissues. Also included in the term are derivatives and fractions of such fluids. The cells may be dissociated, in the case of solid tissues, or tissue sections may be analyzed. Alternatively a lysate of the cells may be prepared.

Diagnosis may be performed by a number of methods to determine the absence or presence or altered amounts of normal or abnormal Bok in patient cells. For example, detection may utilize staining of cells or histological sections, performed in accordance with conventional methods. Cells are permeabilized to stain cytoplasmic molecules. The antibodies of interest are added to the cell sample, and incubated for a period of time sufficient to allow binding to the epitope, usually at least about 10 minutes. The antibody may be labeled with radioisotopes, enzymes, fluorescers, chemiluminescers, or other labels for direct detection. Alternatively, a second stage antibody or reagent is used to amplify the signal. Such reagents are well known in the art. For example, the primary antibody may be conjugated to biotin, with horseradish peroxidase-conjugated avidin added as a second stage reagent. Alternatively, the secondary antibody conjugated to a flourescent compound, e.g. flourescein, rhodamine, Texas red, etc. Final detection uses a substrate that undergoes a color change in the presence of the peroxidase. The absence or presence of antibody binding may be determined by various methods, including flow cytometry of dissociated cells, microscopy, radiography, scintillation counting, etc. Diagnostic screening may also be performed for polymorphisms that are genetically linked to a disease predisposition, particularly through the use of microsatellite markers or single nucleotide polymorphisms. Frequently the microsatellite polymorphism itself is not phenotypically expressed, but is linked to sequences that result in a disease predisposition. However, in some cases the microsatellite sequence itself may affect gene expression. Microsatellite linkage analysis may be performed alone, or in combination with direct detection of polymorphisms, as described above. The use of microsatellite markers for genotyping is well documented. For examples, see Mansfield et al. (1994) Genomics 24:225–233; Ziegle et al. (1992) Genomics 14:1026–1031; Dib et al., supra. It is to be understood that this invention is not limited to the particular methodology, protocols, formulations and reagents described, as such may, of course, vary. It is also to be understood that the terminology used herein is for the purpose of describing particular embodiments only, and is not intended to limit the scope of the present invention which will be limited only by the appended claims.

It must be noted that as used herein and in the appended claims, the singular forms "a", "and", and "the" include plural referents unless the context clearly dictates otherwise. Thus, for example, reference to "a complex" includes a plurality of such complexes and reference to "the formulation" includes reference to one or more formulations and equivalents thereof known to those skilled in the art, and so forth.

Unless defined otherwise, all technical and scientific terms used herein have the same meaning as commonly understood to one of ordinary skill in the art to which this invention belongs. Although any methods, devices and materials similar or equivalent to those described herein can be used in the practice or testing of the invention, the preferred methods, devices and materials are now described.

All publications mentioned herein are incorporated herein by reference for the purpose of describing and disclosing, for example, the methods, ligands, and methodologies that are described in the publications which might be used in connection with the presently described invention. The publications discussed above and throughout the text are provided solely for their disclosure prior to the filing date of the present application. Nothing herein is to be construed as an admission that the inventors are not entitled to antedate such disclosure by virtue of prior invention.

The following examples are put forth so as to provide those of ordinary skill in the art with a complete disclosure and description of how to make and use the subject invention, and are not intended to limit the scope of what is regarded as the invention. Efforts have been made to ensure accuracy with respect to the numbers used (e.g. amounts, temperature, concentrations, etc.) but some experimental errors and deviations should be allowed for. Unless otherwise indicated, parts are parts by weight, molecular weight is average molecular weight, and pressure is at or near atmospheric.

Experimental

EXAMPLE 1

Isolation and Characterization of Bok cDNA

Materials and Methods

Two-Hybrid Screening

The full-length open reading frame (ORF) of rat Mcl-1 cDNA was fused in frame with the GAL4-binding domain (GAL4-BD) into the pGBT-9 yeast shuttle vector (Clontech, Palo Alto, Calif.). This vector was used to identify Mcl-1-interacting proteins by screening 1.5 million transformants from a GAL4-activation domain (AD)-tagged ovarian fusion Matchmaker cDNA library. The ovarian cDNAs were prepared from 27-day-old Sprague-Dawley rats primed for 36 h with 10 IU equine gonadotropin. Yeast cells were first transformed with pGBT9-Mcl-1 and colonies selected in plates deficient for tryptophan. In the second step, cells were transformed with cDNAs from the ovarian library before selection of clones in plates lacking tryptophan, leucine and histidine. Positive transformants were further selected for growth in media containing 5 mM 3-aminotriazole. Individual AD-fusion cDNAs were retrieved following transformation of E. coli cells.

A total of 40 potential Mcl1-interacting clones were re-screened against the empty vector or vector encoding different Bcl-2 proteins to eliminate false positives. Three clones of Bok cDNAs were isolated based on their ability to interact with Mcl-1 in an HF7c yeast reporter strain (Fields & Song (1989) Nature 340, 245–247). DNA sequence analysis and comparison with known genes using the BLASTX algorithm revealed that the positive clones encode a polypeptide sharing high homology with Bclproteins. Further analysis of expressed sequence tags (EST) in the GenBank revealed that EST accession number AA103989 has greater than 98% identity with the 5'-sequence of cloned cDNA and contains extra 5'-sequence of the murine Bok homolog. Full-length ORF and 5'-untranslated sequence of rat Bok were obtained by PCR using the GAL4-AD-tagged ovarian Matchmaker cDNA library as the template and an upstream primer based on murine EST. Complementary DNA fragments with an identical ORF were also obtained in separate PCR using a rat brain cDNA library (Stratagene, La Jolla, Calif.) as the template. Interactions between Bok and different Bclmembers were assessed in the yeast two-hybrid system using pGBT9 GAL4-BD and pGADGH GAL4-AD vectors (Bartel et al. (1993) in Cellular Interaction in Development: A Practical Approach, ed. Hartley, D. A. (Oxford University Press, Oxford), pp. 153–179). Specific binding of different protein pairs was evaluated based on the activation of GAL1-HIS3 and GAL4-lacZ reporter genes.

Cell Culture and Transfection with Plasmids.

For the expression of Bcl-2 proteins in eukaryotic cells, PCR-generated ORF of different cDNAs were subcloned into the pcDNA3 vector (Invitrogen, Inc., San Diego, Calif.). Following transfection of cDNAs, cell death was monitored (Kumar et al. (1994) Genes Dev. 8, 1613–1626). CHO cells ($2 \times 10^5$/well) were cultured in Dulbecco's modified Eagle's medium (DMEM)/F12 supplemented with 10% fetal bovine serum, 100 U/ml penicillin, 100 µg/ml streptomycin and 2 mM glutamine. One day later, cells were transfected using the lipofectamine procedure (Life Technologies, Gaithersburg, Md.) with the empty pcDNA3 expression vector or the same vector containing different cDNAs, together with $\frac{1}{10}$–$\frac{1}{20}$ fractions of an indicator plasmid pCMV-β-gal to allow the identification of transfected cells. Inclusion of 10- to 20-fold excess of expression vectors as compared to the pCMV-β-gal reporter plasmid ensured that most of the β-galactosidase expressing cells also expressed the protein(s) under investigation. Cells were incubated with plasmids in a serum-free medium for 4 h, followed by adding fetal bovine serum to a final concentration of 5% and further incubation for 14 h. After an additional culture in fresh medium for 18 h, cells were fixed by 0.25% glutaraldehyde and stained with X-gal (0.4 mg/ml) to detect β-galactosidase expression. The number of blue cells was counted by microscopic examination (Kumar et al. (1994) Genes Dev. 8, 1613–1626). To verify the nature of cell death, total cellular DNA was extracted for 3"-end labeling of DNA ends at 18 h after transfection with $^{32}$P-ddATP before gel fractionation to identify internucleosomal DNA fragmentation (Hsu et al. (1996) Endocrinology 137, 4837–4843). Statistical differences among treatment groups were analyzed using one-way ANOVA and Scheffe F-test.

Northern and Southern Blots and In Situ Analyses

For Northern blot analysis of Bok expression, tissues were collected from 27-day-old Sprague-Dawley rats (Simonsen Lab, Gilroy, Calif.). For Bok expression in ovarian cells, ovaries were obtained from 26-day-old rats implanted for two days with a diethylstilbestrol capsule to stimulate development of multiple early antral follicles (Bicsak et al. (1986) Endocrinology 119, 2711–2719). Granulosa cells were prepared by needle puncture. For the extraction of total RNA, tissues were homogenized in Tri-Reagent solution (Molecular Research Center, Inc., Cincinnati, Ohio) and at least two pools from each treatment group were used. In addition, poly (A+) RNA was isolated using the Oligotex oligo-dT resin (Qiagen, Inc., Chatsworth, Calif.). Aliquots of each sample were denatured and fractionated in 1% agarose gels containing formaldehyde before northern blotting analysis. Membranes were pre-hybridized for 4 h at 65° C. in a solution containing 50% formamide, 5×sodium phosphate buffer (SSPE), 5×Denhardt's solution, 0.5% SDS and 500 μg/ml yeast tRNA. This was followed by overnight hybridization in the same conditions but with 1×10$^6$ cpm/ml of $^{32}$P-labeled Bok or GAPDH cRNA probe. After hybridization, the membranes were washed twice in 2×SSC, 1% SDS at room temperature, followed by two washes in 0.1×SSC, 1% SDS at 65° C. before exposure to Kodak RX films (Eastman Kodak, Rochester, N.Y.). For studies on the conservation of the Bok gene during evolution, the Zoo blot (Clontech) containing genomic DNA from different vertebrate species was hybridized with a $^{32}$P-labeled rat Bok cDNA probe under stringent conditions.

For in situ hybridization analysis of Bok mRNA expression, ovaries from 26-day-old rats were isolated and fixed at 4° C. for 4 h in 4% paraformaldehyde in PBS (pH 7.4), followed by overnight dehydration in 0.5M sucrose. Tissue blocks were embedded in Tissue-Tek solution (Sakura Finetek USA Inc., Torrence, Calif.) and snapped frozen in liquid nitrogen. Twelve μm thick cryo-sections were mounted on charged microscopic slides (Fischer Scientific, Pittsburgh, Pa.), post-fixed in 4% paraformaldehyde and stored at −70° C. for up to 1 month. Hybridization and washes of cryosections were as previously described (Hsu et al., supra.). After two weeks of exposure under NTB2 emulsion (Kodak), the slides were developed, counter-stained and mounted with Permount (Fisher Scientific, Fair Lawn, N.J.) for observation and photography using a Nikon Optiphot microscope.

Results

Using the anti-apoptotic protein Mcl-1 as bait, we screened an ovarian fusion cDNA library and isolated three Bok clones. Subsequent DNA sequencing and identification of homologous murine ESTs allowed isolation of full-length Bok cDNAs following PCR of ovarian and brain cDNA libraries. The ORF of Bok encoded a protein of 213 amino acids showing no identity with any known gene. The novel protein has a predicted molecular weight of 23.5 kD and a pI of 9.1. The methionine initiation codon conformed to the consensus Kozak sequence and hydrophobicity analysis predicted the presence of a C-terminal transmembrane domain. In addition, two potential phosphorylation sites were found near the N-terminal region. Comparison of DNA sequences among different Bcl-2 proteins indicated that Bok was a novel member of this family showing conserved BH 1, 2 and 3 domains. However, the BH4 domain, known to be important for the anti-apoptotic function of mammalian Bcl-2 proteins, was missing in Bok. Closer comparison indicated the core BH1 domain of Bok (TWGK) was less conserved as compared with other Bcl-2 proteins (NWGR). For the BH3 domain found in pro-apoptotic members, the core sequence (GDE) was conserved in Bok but the flanking sequences were different. Furthermore, analysis of the phylogenetic relatedness of the different Bcl-2 members suggests that, during evolution, Bok diverged early from other Bcl-2 proteins.

We investigated interactions between Bok and different anti- and pro-apoptotic Bcl-2 proteins. Bok only interacts with selective anti-apoptotic Bcl-2 proteins in the yeast two-hybrid system. Yeast cells were grown in the selective media containing 53-aminotriazole and without Trp, Leu and His. Prominent growth of yeast colonies expressing Bok fused to the GAL4 activation domain together with Mcl-1, BHRF1 or Bfl-1 fused to the GAL4 binding domain could be seen. Minimal growth of yeast colonies was found in cells that express the same Bok expressing vector together with Bcl-2, Bcl-xL, Bcl-w, BAD, Bax, Bak or Bik fused to the GAL4 binding domain. In addition, prominent growth of colonies expressing Bcl-xL and different pro-apoptotic Bcl-2 proteins indicated that the lack of growth in yeast cells expressing Bok and different pro-apoptotic family members was not due to suppression of cell growth by these pro-apoptotic proteins.

Of interest, Bok did not interact with any pro-apoptotic members tested. To demonstrate that the lack of interactions between Bok and pro-apoptotic Bcl-2 proteins was not due to the killing of yeast cells by these apoptosis agonists, we also tested the growth of yeast cells co-transformed with Bcl-xL and different pro-apoptotic proteins. Although Bcl-xL showed negligible interaction with Bok, it interacted strongly with all the pro-apoptotic members tested.

To further study the restricted dimerization property of Bok with selective anti-apoptotic proteins, we tested the growth of yeast cells that were co-transformed with different pairs of pro- and anti-apoptotic Bcl-2 proteins. Several pro-apoptotic proteins (Bak, Bik and Bax), unlike Bok, all interacted strongly with diverse anti-apoptotic proteins tested, data shown in Table 1, suggesting the restricted hetero-dimerization property of Bok was unique. [t1]

TABLE 1

| | pGBT-9 | BHRF1 | Mcl-1 | Bfl-1 | Bcl-2 | Bcl-xL | Bcl-w |
|---|---|---|---|---|---|---|---|
| Bok | − − | ++ | ++ | + | − − | − − | − − |
| Bax | − − | ++ | ++ | ++ | ++ | ++ | ++ |
| Bak | − − | ++ | ++ | ++ | ++ | ++ | ++ |
| Bik | − − | ++ | ++ | ++ | ++ | ++ | ++ |

Summary of protein—protein interactions between pairs of pro-apoptotic proteins (Bok, Bak, Bik and Bax) and different anti-apoptotic Bcl-2 members. The positive signs indicate prominent (++) or moderate (+) yeast cell growth whereas the negative signs (−) indicate the absence of reporter gene expression.

The ability of Bok to regulate apoptosis in mammalian cells was investigated. In CHO cells, transfection with expression vectors encoding Bok for 36 h induced cell death. The pro-apoptotic effect of Bok was specific because transfection of the empty plasmid or the same plasmid containing Bok cDNA in reverse orientation did not affect cell survival. Furthermore, co-expression of P35, a cysteine protease inhibitor derived from the baculovirus (Bump et al. (1995) Science 269, 1885–1888), prevented Bok-induced cell killing as indicated by increases in the number of viable cells.

Normal cell morphology was found in cells transiently transfected with the empty pcDNA3 expression vector (2.1 μg DNA/35 mm dish) or the vector containing Bok cDNA in reverse orientation. Cells were also transfected with the Bok expression vector without or with an equal amount of the P35-expressing construct.

The 3"-end labeling of genomic DNA fragments at an earlier time point (18 h) further demonstrated the induction of internucleosomal DNA fragmentation following Bok over-expression, confirming the induction of apoptosis. The observed DNA fragmentation was blocked by co-expression with P35. CHO cells were treated as described in above. At 18 h after transfection, cellular DNA was extracted for analysis of DNA fragmentation using a 3"-end labeling method.

Quantitative analysis also indicated that Bok over-expression decreased viable cell number by 75% whereas co-expression of P35 completely reversed Bok killing (Fig. substantiating the involvement of caspases in Bok action.

Figure 2:
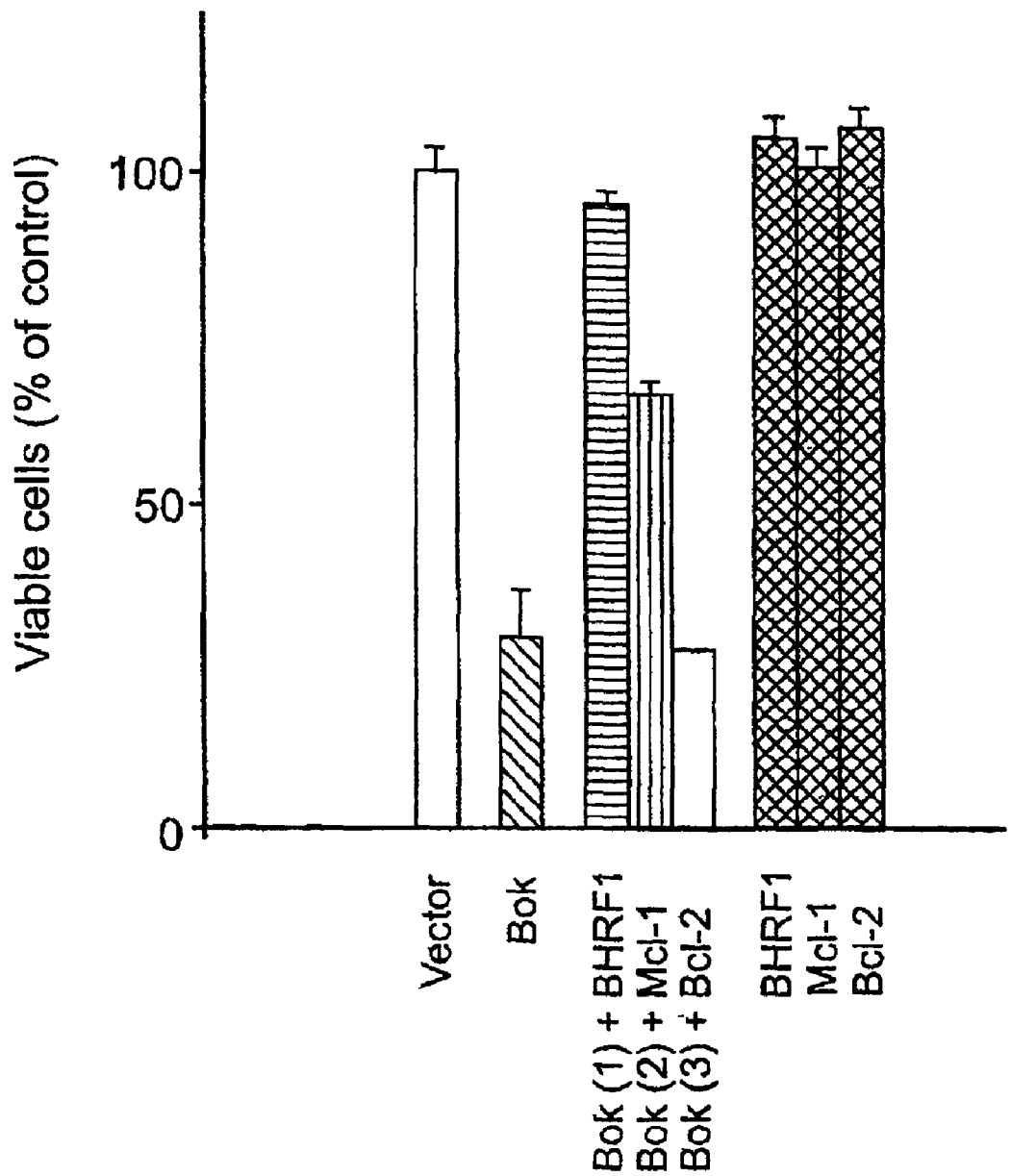
FIG. 2 is a graph showing suppression of Bok-induced apoptosis by selective anti-apoptotic Bcl-2 members in CHO cells. Cell killing by Bok and the antagonistic effects of Mcl-1 and BHRF1 were analyzed. Cell transfection and estimation of apoptosis were as described for FIG. 1. Co-expression of Bcl-2 was ineffective in suppressing Bok-induced apoptosis.

We further tested if the restricted hetero-dimerization of Bok with selective anti-apoptotic Bcl-2 members found in the yeast two-hybrid system could be substantiated in mammalian cells. Bok was co-expressed with Mcl-1, BHRF1 or Bcl-2 in CHO cells. As shown in FIG. 2, Bok-induced apoptosis was attenuated following co-expression with Mcl-1 or BHRF1; but co-expression with Bcl-2 was ineffective in blocking Bok action. Transfection of the same Bcl-2 expression vector was, however, capable of blocking apoptosis induced by staurosporin.

The expression of Bok mRNA in diverse rat tissues was examined. High levels of Bok transcript of ~1.5 kb in size were abundant in the ovary, testis and uterus, less abundant in the brain, heart and intestine and negligible in other tissues examined. Further analysis of Bok mRNA in isolated granulosa cells demonstrate high levels of expression in these cells that undergo apoptosis during follicle degeneration. In situ hybridization analyses further confirmed high levels of the Bok transcript in the granulosa cells of antral and preantral follicles, with minimal signals in theca and interstitial cellsFor northern blot analysis, poly (A)+-selected RNA from different tissues of rats at 27 days of age or from isolated granulosa cells of estrogen-treated rats were hybridized with a $^{32}$P-labeled Bok cRNA probe. After washing, the blots were exposed to X-ray films at −70° C. for five days. Subsequent hybridization with a GAPDH cRNA probe was performed to estimate nucleic acid loading (8 h exposure). For in situ hybridization analysis, ovaries from immature eCG-treated rats were probed with the anti-sense Bok cRNA. Positive signals were found in granulosa cells of preantral follicles and an antral follicle. No signal was found in a section hybridized with the sense Bok probe.

Conservation of the Bok gene in diverse vertebrates was tested using Southern blot hybridization of genomic DNA from different species. DNA was digested with the EcoRI enzyme and probed with a Bok cDNA probe. Following hybridization at 68° C., the membrane was washed under high stringency conditions (1% SDS, 0.1×SSC at 65° C.) before exposure. Under high stringency washing conditions, the rat cDNA cross-hybridized strongly with rat, human and monkey genomic DNA and weakly with dog, cow and rabbit DNA. Negligible hybridization signals were found for chicken DNA.

A cDNA encoding the human bok gene was isolated from a human ovary cDNA library. A partial sequence of the human protein is provided in SEQ ID NO:3.

Discussion

A new pro-apoptotic Bcl-2-related protein Bok has been identified based on its binding to an ovarian anti-apoptosis protein Mcl-1. In addition to its elevated expression in several reproductive tissues, Bok was found in diverse other tissues. In addition, Bok shows a selective hetero-dimerization property by interacting with some (Mcl-1, BHRF1 and Bfl-1) but not other (Bcl-2, Bcl-xL and Bcl-w) anti-apoptotic proteins. Coupled with findings that Bok-induced apoptosis could only be antagonized by selective anti-apoptotic proteins, the present data suggest that different pro- and anti-apoptotic Bcl-2 protein pairs may play tissue-specific roles in the regulation of apoptosis. Due to the higher expression of Bok to ovarian granulosa cells and several reproductive tissues characterized by hormonally regulated cyclic cell turnover, further analyses of Bok action in the gonads and uterus could provide unique models to study the hormonal regulation of apoptosis. Because most of the Bcl-2-related proteins have been identified in the lymphoid system, the present yeast two-hybrid screen provides an experimental paradigm to isolate novel Bcl-2 homologs essential for apoptosis regulation in other tissues.

Although the mechanism by which the Bcl-2 proteins participates in the "decision" step of apoptosis is not clear, the ratio of anti- and pro-apoptotic Bcl-2 members and their hetero- and homo-dimerization are believed to determine whether a cell will respond to an apoptotic signal. Among the Bcl-2 family of proteins, several homology domains have been found to be essential for their function. Bok contains conserved BH1, 2 and 3 domains but lacks the BH4 domain found in most anti-apoptotic members. In addition, the conserved NH1 region important for the survival function of several anti-apoptotic Bcl-2 proteins is also absent in Bok. Consistent with its structural features, over-expression of Bok in CHO cells induces apoptosis based on observed cell morphology and internucleosomal DNA fragmentation. Bok-induced cell killing, like that induced by Bax and BAD, is mediated by caspases as demonstrated by the suppressive actions of the baculoviral P35 protein.

Among the pro-apoptotic Bcl-2 proteins, Bok is most similar to Bax and Bak in having the BH1, 2 and 3 domains plus the C-terminal transmembrane sequence. Studies on Bax and Bak with truncation in different BH domains suggested that these pro-apoptotic proteins might exert their effects by hetero-dimerizing with Bcl-2 or Bcl-xL. Competitive dimerization between selective pairs of anti- and pro-apoptotic Bcl-2 proteins is believed to be involved in the "decision" step of apoptosis. Furthermore, interactions among the Bcl-2 family of proteins appear to exhibit a defined selectivity and hierarchy. For example, the anti-apoptotic E1B protein shows preferential binding to pro-apoptotic Bcl-2 proteins, whereas the pro-apoptotic Hrk binds only to the anti-apoptotic family member. Thus, the pro-apoptotic protein Bok may regulate apoptosis through similar mechanisms by forming hetero-dimers with selective anti-apoptotic proteins.

Analysis of the relatedness of amino acid sequences of different Bcl-2 proteins indicated that Bok is not closely related to any particular Bcl-2 member and probably diverged early during evolution. The less conserved BH1 domain of Bok may determine its unique hetero-dimerization property. In both yeast and mammalian cells, Bok interacts with some but not other anti-apoptotic proteins, suggesting the possible evolution of selective pairs of death agonists and antagonists with restricted hetero-dimerization properties to confer tissue specificity of the death program. Apoptosis induced by Bok in transfected CHO cells could be mediated through inhibition of the protection afforded by Mcl-1 or other Bok partners. It is likely that Bok may interact with its dimerization partner(s) including Mcl-1 and Bfl-1 in reproductive tissues to regulate apoptosis. Of interest, our recent data indicated that Mcl-1, but not Bcl-2, is highly expressed in ovarian cells. Based on the suppression of Bok-induced apoptosis by BHRF1, it is possible that reproductive tissues expressing Bok are potential targets for this anti-apoptotic protein encoded by the Epstein-Barr virus. Recent studies have suggested that anti-apoptotic proteins may bind to ced-4/Apaf-1 homologs, which, in turn, activate downstream caspases. Elucidation of the hetero-dimerization partner(s) for Bok in gonads and uterus would allow characterization of the putative ced-4 homologs in these tissues.

Recent crystallographic analyses of complexes formed between the anti-apoptotic protein Bcl-xL and the BH3 domain of the pro-apoptotic Bak indicated that the α-helix in the BH3 domain of different Bcl-2 proteins plays a central role in defining the binding specificity to Bcl-xL. Because Bok does not interact with Bcl-xL in the yeast two-hybrid system, further studies on the BH3 region of Bok and related proteins could define the specificity of hetero-dimerization among different pro- and anti-apoptotic protein pairs and their role in apoptosis regulation.

Although over-expression of Bax and Bak induces yeast cell death, the present Bok fusion protein did not affect yeast cell survival. In addition, lack of interactions between Bok and different pro-apoptotic Bcl-2 proteins in the two-hybrid assay are not due to detrimental effects of these death agonists on yeast cells because co-transformation of these apoptosis agonists with Bcl-xL led to activation of the reporter genes. It is likely that moderate expression of these death agonists using the present expression vector may not significantly affect yeast cell survival, thus allowing studies on interactions between different Bcl-2 proteins.

The majority of ovarian follicles and about 50% of testicular germ cells undergo apoptosis under normal physiological conditions, whereas the menstruation involves monthly apoptosis of uterine endometrial cells. The restricted expression of Bok in the gonads and uterus suggests its potential role in the regulation of apoptosis in these tissues. It is likely that selective pairs of Bcl-2 agonists/antagonists may play tissue-specific roles in the regulation of apoptosis. Indeed, mutant mice deficient in Bcl-2 or Bax showed abnormality in apoptosis regulation only in distinct cell lineage. Although Bax-deficient mice showed an accumulation of granulosa cells in atretic follicles, these cells were still apoptotic, suggesting the involvement of additional pro-apoptotic factors during ovarian follicle atresia. Because the pro-apoptotic protein Bax has been suggested to function as a tumor suppressor gene in colon adenocarcinomas and because inactivation of Bax in transgenic mice leads to enhanced tumorigenesis, it would also be interesting to investigate changes in Bok function during gonadal and uterine tumorigenesis. Because cyclic variations in reproductive hormones are essential in the regulation of apoptosis in gonadal and uterine tissues, future investigations on the hormonal regulation of the Bok and its dimerization partner (s) in these reproductive tissues would allow the design of novel strategies to modulate reproductive functions. These studies could also provide understanding on the role of Bok in gonadal and uterine diseases associated with aberrant regulation of apoptosis.

EXAMPLE 2

Characterization of a Bok Splicing Variant with a Truncated BH3 Domain, which Induces Apoptosis but Does Not Dimerize with Anti-Apoptotic Bcl-2 Proteins A Bok splicing variant is identified in which the region encoded by exon three is absent, creating a truncated short form (Bok-S) of the full-length Bok protein (Bok-L). The skipping of exon three maintains the original reading frame and retains the BH2 and the C-terminal membrane anchoring domains; however, parts of the BH3 and BH1 domains were deleted. Functional analysis indicated that Bok-S is still capable of inducing apoptosis. The truncated Bok has lost its ability to heterodimerize with Mcl-1, BHRF-1 and Bfl-1, suggesting that the proapoptotic activity of this variant is not mediated by its binding to antiapoptotic Bcl-2 proteins.

Materials and Methods

Reverse Transcription-PCR of the Bok-S Transcript

Total RNA from different tissues was isolated from 27-day-old Sprague-Dawley rats using an anion exchange resin chromatographic column (Qiagen, Chatsworth, Calif.) before reverse transcription with oligo (dT) 18 as primer in a reaction containing RNase H-free reverse transcriptase from Moloney murine leukemia virus (Clontech, Palo Alto, Calif.). For PCR amplification of Bok cDNAs, aliquots of DNA equivalent to 0.5 µg total RNA were used in each reaction (50 µl). To minimize contamination during PCR, control reactions containing a single primer or RNA without reverse transcriptase were routinely performed. All PCR was carried out under high stringency conditions (94° C., 45 s, 68° C. 45 s, 72° C. 4 min) for 30 cycles. Isolation of Bok genomic DNA, Southern blot hybridization and genomic analysis. A genomic DNA fragment was isolated from a mouse BAC genomic DNA library (Genome Systems Inc., St. Louis, Mo.) using the full-length Bok cDNA probe. The Bok genomic fragment was first analyzed by restriction enzyme mapping, followed by subcloning into the pUC18 vector for dideoxy sequencing analysis of both DNA strands. Overlapping clones were isolated to define the direction of individual clones and to facilitate assignment of intron-exon junctions. For Southern blot hybridization analysis, genomic DNA (10 µg) was digested with indicated restriction enzymes, separated by electrophoresis on a 0.8% Agarose gel, and then transferred onto a Nylon membrane (Hybond-N, Amersham Corp., Arlington Heights, Ill.). Hybridization was performed in the QuickHyb buffer (Clontech) at 60 C with $^{32}$P-labeled cDNA probes. The filters were washed with 0.1×SSC and 0.5% SDS at 65 C. before exposure. Generation of mutant constructs. Specific mutations in the BH3 domain of Bok-L were generated by a two-step PCR mutagenesis method using a Bok cDNA template as previously described (Hsu et al. (1997) Mol Endocrinol 11: 1858–1867). The resulting PCR products were evaluated for correct size on a 1% Agarose gel, purified, and subcloned into the EcoR1 site of the pcDNA3 vector for mammalian cell expression (Invitrogen, Inc., San Diego, Calif.). Truncated Bax and Bak constructs (Bax-S and Bak-S) with homologous deletion of the BH3-BH1 region found in Bok-S were also generated using two-step overlapping PCR, and subcloned into the EcoRV site of the pcDNA3 vector for eukaryotic cell expression (Hsu et al. supra.) For the yeast two-hybrid assay, mutant Bok-L cDNAs were subcloned into the pGADGH expression vector. Restriction mapping and dideoxy sequencing confirmed proper orientation and the authenticity of the inserts.

Yeast Two-Hybrid Assay

To study dimerization between different Bcl-2 family proteins and variants or mutants of Bok, cDNAs for Bok-L, Bok-S or Bok mutants were fused to the activation domain (AD) of GAL4 in a yeast shuttle vector pGADGH. Complementary DNAs encoding different Bcl-2 proteins were fused to the GAL4-binding domain (BD) of pGBT9. After transformation of yeast cells, colonies containing different protein pairs were selected on plates lacking tryptophan and leucine. To test for specific protein—protein interactions, positive transformants were further selected for growth in media deficient for tryptophan, leucine and histidine but containing 5–30 mM 3-aminotriazole to inhibit endogenous histidine production. A minimum of five independent transformants containing each pair of fusion cDNAs was routinely analyzed.

Analysis of Apoptosis in Transfected CHO Cells

Apoptosis was monitored following transfection of different cDNAs as previously described ( Hsu et al. (1997)

Proc. Natl. Acad. Sci. USA 94: 12401 CHO cells ($2 \times 10^5$ cells/well) were cultured in Dulbecco's modified Eagle's medium (DMEM)/F12 supplemented with 10% fetal bovine serum, 100 U/ml penicillin, 100 g/ml streptomycin and 2 mM glutamine. One day later, cells were transfected using the lipofectamine procedure (Life Technologies, Gaithersburg, Md.) with the pcDNA3 expression vector with or without different cDNA inserts, together with 1/10 to 1/20 amounts of an indicator plasmid pCMV-β-gal to allow the identification of transfected cells. Inclusion of a 10-fold excess of expression vectors as compared with the pCMV-β-gal reporter plasmid ensured that most of the β-galactosidase-expressing cells also expressed the protein (s) under investigation. Cells were incubated with plasmids in a serum-free medium for 4 h, followed by the addition of fetal bovine serum to a final concentration of 5% and further incubation for 14 h. After an additional culture in fresh medium for 18 h, cells were fixed by using 0.25% glutaraldehyde and stained with X-gal to detect β-galactosidase expression. The number of blue cells was counted by microscopic examination. Data are expressed as the percentage (mean +/–SEM) of viable cells as compared to the control group. In vitro direct protein-binding assay. To further demonstrate the specificity of interactions between Bok variants and antiapoptotic proteins, direct protein— protein interactions were studied using recombinant Bok and FLAG-tagged BHRF-1 translated in vitro. $^{35}$S-methionine labeled or nonlabeled proteins were generated using the TNT coupled reticulocyte lysate system (Promega, Madison, Wis.). Pairs of proteins were incubated in the binding buffer (PBS, 0.2% NP-40 and protease inhibitor cocktail; Sigma, St. Louis, Mo.) for 2 h at 4° C. followed by incubation with 1.5 μg of M2 antibody against the FLAG tag (Kodak, Rochester, N.Y.) under gentle agitation. The complexes formed between the antibody and recombinant proteins were precipitated with Protein A Sepharose (Pharmacia Biotech, Uppsala, Sweden) and resolved using 12–15% SDS PAGE. Following fixation, gels were treated with Amplify fluorographic agents (Amersham Life Science Inc., England) before exposure to x-ray films.

Statistical Analyses and Sequence Analysis.

One-way analysis of variance followed by Scheffe's F-test was used to determine the statistical significance of cell viability employing the STATVIEW software (Abacus Concepts, Inc., Berkeley, Calif.). The hydropathicity of protein sequence was analyzed using Biology Workbench version 2.0 (http://biology.ncsa.uiuc.edu/BW/BW.cgi).

Results

Existence of Long and Short Bok Splicing Variants in Reproductive Tissues

We amplified Bok cDNA from a rat ovarian cDNA library using primers flanking the open reading frame (ORF) of Bok. A 513 bp PCR product was obtained in addition to the predicted 642 bp band. DNA sequencing of the lower molecular weight product indicated it was identical to that of the Bok cDNA except that nucleotides encoding amino acid 76-118 were missing. This short transcript (Bok-S) encoded a 170 amino acid polypeptide and the deletion of 43 amino acids from the full-length 213 amino acid protein (Bok-L) led to the fusion of the N-terminal half of the BH3 domain to the C-terminal half of the BH1 domain. To confirm the authenticity of this variant, reverse transcription-PCR was performed using total RNA from different tissues. Electrophoresis analysis confirmed the presence of a PCR product of 642 bp in the ovary, uterus and testis, tissues known to express the Bok transcript. In addition, a lower band of 513 bp was found in the ovary, less in the uterus and absent from the testis. Negative control reactions using only a single primer or RNA without reverse transcription did not generate any products. Subsequent subcloning and sequencing confirmed that the 642 bp and 513 bp bands encode the expected Bok-L and Bok-S transcripts, respectively.

The deduced amino acid sequence of Bok-S showed that a presumptive alternative splicing led to the disruption of both BH1 and BH3 domains of Bok-L, changing the original BH3 sequence [SEQ ID NO:9] 71 LLRLGDELEQIR 82 to [SEQ ID NO:10] 71 LLRLGITWGKW 82. However, Kyte-Doolittle hydropathicity analysis suggested that the hydropathicity profile of the BH3/BH1 fusion region found in Bok-S did not differ substantially from that of the original BH1 domain in Bok-L. Furthermore, the 5 and 6 regions predicted, based on their homology to similar regions in Bax and Bak, were unaltered in the truncated Bok-S. These regions have been postulated to be important for channel formation in the mitochondria by different Bcl-2 proteins.

Bok Gene Arrangement and the Derivation of Alternative Splicing Variants.

To elucidate the mechanism by which two Bok isoforms were generated, the Bok gene and its exon/intron junctions were analyzed. Following the screening of a bacterial artificial chromosome-based mouse genomic DNA library using a mouse Bok cDNA fragment, one genomic clone for Bok was isolated. The amino acid sequence of the coding region for the mouse clone was found to be identical to its rat counterpart. Southern blot hybridization of mouse genomic DNA digested with different restriction enzymes using cDNA probes corresponding to two different regions of the Bok gene demonstrated the presence of a single Bok gene in the mouse. Further characterization of the genomic clone indicated that the entire Bok gene spanned 11 kb and consisted of 5 exons. The Bok ORF was encoded by sequences in exons II to V whereas exon I contained only untranslated sequences. Comparison of the ORF of Bok-S with genomic sequences indicated that Bok-S was derived following the splicing out of exon III.

Bok-S Promotes Cell Death in Transfected Cells.

To study the role of Bok-S in apoptosis regulation, expression vectors containing Bok-S in either sense or antisense orientation were constructed. Transfection of CHO cells with either Bok-S or Bok-L, but not the reverse construct, significantly reduced the number of transfected cells, demonstrating that Bok-S retained its ability to induce apoptosis despite the loss of the BH3 sequence. In addition, cell killing induced by either Bok-S or Bok-L was antagonized by cotransfection with P35, a baculoviral-derived caspase inhibitor. Bok-S does not heterodimerize with antiapoptotic Bcl-2 proteins. Because Bok was isolated based on its ability to bind Mcl-1 and the dimerization between pro- and antiapoptotic Bcl-2 proteins has been suggested to be important in apoptosis, we analyzed whether Bok-S that maintained its cell killing ability could still dimerize with antiapoptotic Bcl-2 proteins. In the two-hybrid assay, interactions between Bok-S and different Bcl-2 family members were tested. Bok-S did not interact with any Bcl-2 proteins tested whereas Bok-L interacted strongly with Mcl-1, Bfl-1 and BHRF-1, as previously reported. To further confirm findings in yeasts, a direct protein—protein interaction assay was performed using in vitro translated recombinant Bok variants and the antiapoptotic protein BHRF-1 that exhibited strongest interaction with Bok-L in yeast. BHRF-1 interacted strongly with Bok-L in vitro but showed negligible interaction with Bok-S. Thus, heterodimerization of Bok-S with antiapoptotic Bcl-2 proteins is probably not needed for apoptosis induction.

BH3 Mutants of Bok Defective in Heterodimerization Still Retain Proapoptotic Activity.

Because Bok-S lacking a BH3 domain still retained its cell killing potential, we hypothesized that the BH3 domain might be dispensable for the proapoptotic activity of Bok-L. Bok-L cDNAs with alanine or glycine substitutions in the BH3 domain were constructed and the ability of these mutants to promote apoptosis was studied. The mutants included alanine substitutions at the highly conserved glycine 75 or glycine 75 plus flanking aspartic acid 76 and glutamic acid 77 (BokADE: G 75 A and BokAAA: 75 AAA 77). In addition, a glycine substitution was made for leucine 71 to leucine 74 (BokGGGG: 71 LLRL 74 to 71 GGGG 74). Transfection of these Bok-L mutants reduced the number of viable CHO cells as compared to the group with cells transfected with the pcDNA3 vector without an insert. In contrast, constructs with mutant cDNAs in reverse orientation had no effect on cell survival. These data suggested that the BH3 domain in Bok-L is dispensable for apoptosis induction. We further tested the ability of these BH3 domain mutants of Bok-L to dimerize with antiapoptotic Bcl-2 proteins in the yeast two-hybrid assay. Substitution of residues in the BH3 domain of Bok-L abolished its interaction with Mcl-1 or Bfl-1. In addition, the ability of Bok-L to interact with BHRF-1 was also abated by glycine substitution at residues 71–74 of Bok-L. Similar to findings using the two-hybrid assay, in vitro translated BokGGGG mutant also lost its ability to interact with Bok-L effectively in the direct protein—protein interaction test. These data suggested that the cell killing ability of these BH3 mutants is not correlated to their ability to dimerize with antiapoptotic Bclproteins.

Mutants of Bax and Bak with Deletion of Their BH3 Domain Resembling Bok-S also Retain Proapoptotic Activity.

Figure 3:
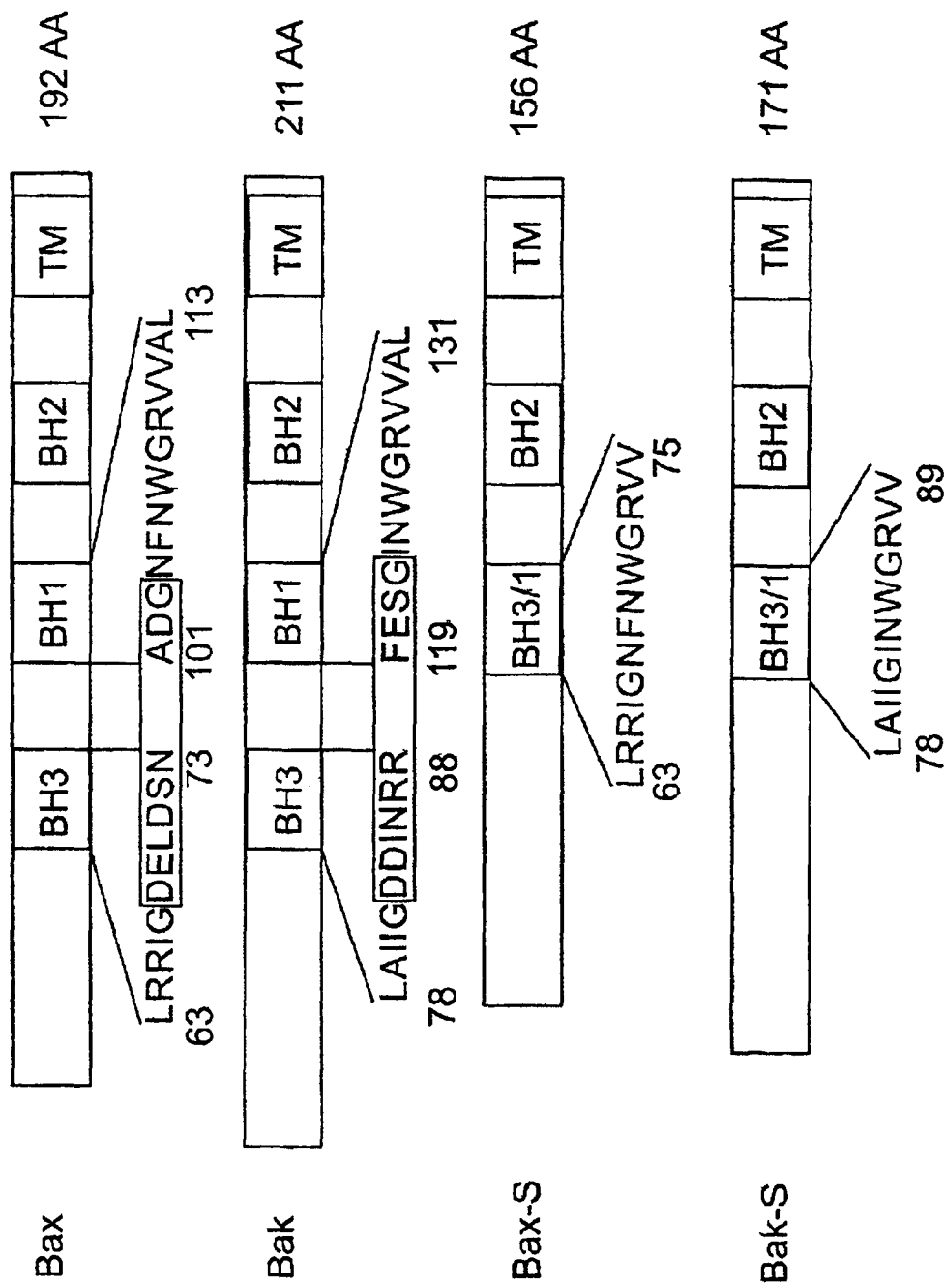
FIG. 3 is a schematic representation of wild type Bax and Bak together with Bax-S and Bak-S constructs with BH3-BH1 deletions similar to that found in Bok-S. The BH domains are boxed and the junctional sequences derived from the fusion of BH3 and BH1 domains (BH3/1) in the mutants are also shown. Numbering of amino acid in the BH1, BH3 and BH3/1 domains are indicated at the bottom of amino acid residues.

Because Bok-L is similar in structure to two other proapoptotic proteins Bax and Bak, deletion mutants with truncation of the BH3-BH1 region similar to that found in Bok-S were constructed for these proteins and named as Bax-S and Bak-S (FIG. 3). Full-length Bak and Bax, like Bok-L and Bok-S, effectively reduced cell viability in the CHO cell transfection assay. Of interest, overexpression of Bax-S or Bak-S also significantly reduced the viability of transfected cells, suggesting that the BH3-BH1 regions deleted in these two proapoptotic proteins are not essential for apoptosis induction.

Discussion

A naturally occurring variant of Bok with proapoptotic activity but exhibiting negligible dimerization with antiapoptotic Bcl-2 members is identified. Bok-S with a 43-amino acid deletion between the BH3 and BH1 domains was likely the result of alternative mRNA splicing, leading to the skipping of exon three during post-transcriptional modification. Analysis of Bok variants and Bok mutants with alterations in the BH3 domain indicated that the BH3 domain of Bok-L is critical for heterodimerization but dispensable for apoptosis induction. Likewise, similar deletions between BH3 and BH1 domains of the homologous proapoptotic proteins Bax and Bak also retained cell killing ability. Thus, Bok-L could promote apoptosis independent of heterodimerization and Bok-S represents a novel proapoptotic Bcl-2 member capable of inducing cell death without binding to or interference by antiapoptotic Bcl-2 partners. This functional Bok variant with retention of the region spanning BH1 and BH2 domains and the TM sequence provides a unique model for further studies of apoptosis mechanisms regulated by Bcl-2 family proteins.

The bifunctional antiapoptotic Bcl-2 proteins play a pivotal role in the decision step of apoptosis. These proteins, represented by Bcl-xL, maintain a channel structure important in the control of mitochondrial membrane potential and volume homeostasis. Regulation of these channels controls the release of cytochrome C essential for the activation of Apaf-1 and caspases important for apoptosis execution. The antiapoptotic Bcl-2 proteins also function as docking proteins for proapoptotic Bcl-2 members. Because several mutants of Bcl-2 and Bcl-xL simultaneously lost antiapoptotic activity and the ability to bind proapoptotic Bcl-2 proteins, it is believed that dimerization of Bclprotein pairs mediated by the consensus BH domains is important in apoptosis regulation. Crystallographic studies and computer modeling showed that the conserved BH1, BH2 and BH3 domains of Bcl-xL and related proteins constitute an elongated hydrophobic cleft capable of interaction with the amphipathic helix formed by BH3 domains of proapoptotic partners. Upon heterodimerization, anti- and proapoptotic Bclpartners antagonize the actions of the other. It is likely that one of the mechanisms by which Bok-L exerts its proapoptotic action is through dimerization with antiapoptotic partners.

Mammalian proapoptotic Bcl-2 proteins can be divided into two subgroups based on domain arrangement. Together with Bax and Bak, Bok-L belongs to the first subgroup showing the conserved BH1, BH2, BH3 and TM domains. In contrast, members of the second subgroup (BAD, BID, Hrk/DP5, Bik/Nbk and Bim) possess only the BH3 domain, with or without the TM region. Earlier studies suggested that proapoptotic proteins function by antagonizing the action of antiapoptotic proteins mediated by BH3 domains. Mutations in the BH3 domain of proapoptotic proteins abolished their dimerization with antiapoptotic partners and cell killing activity. In addition, polypeptides containing minimal BH3 domain sequences bind antiapoptotic proteins and induce apoptosis in transfected cells or cell-free systems. More recent studies, however, demonstrated that Bax, like Bcl-xL and Bcl-2, also shows intrinsic ion channel activity in the artificial membrane. In addition, mutations in the BH1, 2 or 3 domains of Bax do not affect its ability to promote apoptosis. Likewise, Bak mutants accelerate chemotherapy-induced apoptosis independent of its heterodimerization property. These data suggest that the first subgroup of proapoptotic proteins, including Bax, Bak and Bok, could induce apoptosis through channel formation in addition to their role as ligands for antiapoptotic Bcl-2 proteins. Because the second BH3-only subgroup members lack the region spanning BH1 and BH2 domains important for pore formation and mainly reside in the cytoplasm, they are believed to serve as ligands or facilitators of the pore forming Bcl-2 proteins.

Our findings that substitution of conserved residues in the BH3 domain of Bok-L abates its ability to dimerize with antiapoptotic proteins are in accord with studies on the BH3 domain of its proapoptotic homologues. Similarly, truncation of the conserved BH3 domain in the naturally-occurring Bok-S variant also disrupted heterodimerization but retained cell killing ability, indicating the BH3 domain is dispensable for apoptosis induction. Thus, Bok-S represents a new form of proapoptotic protein consisting of only minimal functional modules and manifesting proapoptotic action without direct interactions with antiapoptotic proteins. As shown in the above data, truncation of the region between BH3 and BH1 from Bok-L does not affect the homologous α5 and α6 regions proposed to be important for channel formation in Bax. In addition, the hydropathicity property between the 5"-end of the BH1 region and the C-terminal TM domain is not altered by the truncation found in Bok-S. It is likely that the BH3/1, BH2 and TM domains found in Bok-S comprise a module sufficient for mediating apoptosis through a heterodimerization-independent pathway. Future studies on the channel-forming property of the naturally-occurring Bok-S and other channel-forming Bcl-2 proteins are important for understanding the mechanisms of apoptosis. The channel-forming hypothesis is further supported by the finding that Bax-S and Bak-S with truncation at the BH3-BH1 regions homologous to that of Bok-S also retain proapoptotic activity. Recent studies also indicated that, during apoptosis, activated caspases cleave the N-terminal BH4 domain of antiapoptotic proteins Bcl-2 and Bcl-xL to yield truncated molecules resembling the proapoptotic Bax, Bak or Bok in terms of the BH domain arrangement. Of interest, deletion of the BH4 domain from these antiapoptotic proteins confers proapoptotic activity and mitochondrial release of cytochrome C, presumably mediated through the C-terminal channel-forming region.

Like Bok, splicing variants have been reported for Bcl-2, Bcl-x and Bax genes. The Bcl-xL gene encodes three different variants, each with a distinct function; the long form of Bcl-x (L) exhibits antiapoptotic activity whereas Bcl-x-short and Bcl-x- are proapoptotic. Also, Bcl-2 variants lacking the TM domain show decreased antiapoptotic activity. The proapoptotic Bax gene also encodes a number of splicing variants with unknown function.

At least three mechanisms could be proposed for the action of proapoptotic Bcl-2 proteins: 1) The subgroup of proapoptotic proteins with only the BH3 domain (e.g. the soluble BAD protein) heterodimerizes with membrane-bound antiapoptotic proteins to regulate apoptosis; 2) The subgroup of membrane-bound proapoptotic proteins with BH1, BH2, BH3 and TM domains, represented by Bok-L, heterodimerizes with antiapoptotic proteins (Mcl-1/Bfl-1) or functions as mitochondrial channels to regulate apoptosis; and 3) The unique Bok-S variant does not dimerize with antiapoptotic proteins but probably forms mitochondrial channels to regulate apoptosis. Because Bok-S does not interact with antiapoptotic proteins, apoptosis mediated through Bok-S may be important in situations when unwanted cells need to be eliminated quickly despite the presence of antiapoptotic proteins in the same cell. In the ovary and uterus known to express high levels of Bok transcripts, Bok-S expression could provide a short circuit to promote cell demise in hormone-dependent cell populations that express abundant antiapoptotic proteins (such as Mcl-1) but have to be removed swiftly due to cyclic cell turnover during reproductive cycles. The search for novel death promoters that interact specifically with proapoptotic Bcl-2 proteins could also be simplified based on the lack of interaction between Bok-S and other Bcl-2 proteins. Further characterization of this unique proapoptotic protein would allow a better understanding of intracellular mechanism of apoptosis, particularly for hormone-regulated cell death.

What is claimed is:

1. A process of screening for biologically active agents that mimic Bok function, comprising:
   combining a candidate biologically active agent with a mammalian Bok polypeptide wherein said polypeptide is encoded by a nucleic acid having at least 75% sequence identity to SEQ ID NO:1, SEQ ID NO:3, SEQ ID NO:5, or SEQ ID NO:7 and wherein said polypeptide induces apotosis;
   determining whether said agent competes with said Bok polypeptide in an in vitro assay designed to assess Bok polypeptide activity.

2. A process of screening for biologically active agents that affect Bok function, comprising:
   combining a candidate biologically active agent with a mammalian Bok polypeptide wherein said polypeptide is encoded by a nucleic acid having at least 75% sequence identity to SEQ ID NO:1, SEQ ID NO:3, SEQ ID NO:5, or SEQ ID NO:7 and wherein said polypeptide induces apoptosis; and
   determining whether said agent binds to or interacts with said Bok polypeptide.

3. The process of claim 2 further comprising the step of determining whether said agent up-regulates, down-regulates, enhances, inhibits or modulates the activity of said Bok polypeptide.

4. The process of claim 2 further comprising the step of determining whether said agent enhances, inhibits or modulates apoptosis.

5. The process of claim 3 or claim 4 wherein said agents' effect on the activity of said Bok polypeptide is determined in an in vitro assay or in vivo.

6. The process of any of claims 1 to 4 wherein the Bok polypeptide is a human Bok polypeptide.

7. The process of any of claims 1 to 4 wherein said agent binds to a BH domain of a Bok polypeptide.

8. The process of claim 7 wherein the BH domain is the BH3 domain.

9. The process of any of claims 1 to 4, wherein the Bok polypeptide comprises the amino acid sequence as set forth in SEQ ID NO:2, SEQ ID NO:4, SEQ ID NO:6, or SEQ ID NO:8.

10. The process of any of claims 1 to 4, wherein said agent inhibits the ability of a Bok protein to form heterodimers with anti-apoptotic proteins.

* * * * *